US006884758B2

(12) United States Patent
Giencke et al.

(10) Patent No.: US 6,884,758 B2
(45) Date of Patent: Apr. 26, 2005

(54) 2,4-DIAMINO-1,3,5-TRIAZINES, THEIR PREPARATION, AND THEIR USE AS HERBICIDES AND PLANT GROWTH REGULATORS

(75) Inventors: Wolfgang Giencke, Hofheim (DE); Klemens Minn, Hattersheim (DE); Lothar Willms, Hofheim (DE); Thomas Auler, Kelsterbach (DE); Hermann Bieringer, Eppstein (DE); Christopher Rosinger, Hofheim (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 10/227,760

(22) Filed: Aug. 26, 2002

(65) Prior Publication Data

US 2003/0162661 A1 Aug. 28, 2003

Related U.S. Application Data

(63) Continuation of application No. 10/024,425, filed on Dec. 18, 2001, now abandoned, which is a continuation of application No. 09/332,222, filed on Jun. 14, 1999, now abandoned.

(30) Foreign Application Priority Data

Jun. 16, 1998 (DE) .......................... 198 26 670

(51) Int. Cl.$^7$ ................... C07D 251/44; C07D 251/48; C07D 251/52; A01N 43/66; A01N 43/68
(52) U.S. Cl. ..................... 504/230; 504/231; 544/208; 544/209
(58) Field of Search ............... 544/208, 209, 544/230, 231, 233

(56) References Cited

U.S. PATENT DOCUMENTS

| | | |
|---|---|---|
| 3,183,230 A | 5/1965 | Shapiro et al. |
| 4,523,947 A | 6/1985 | Szczepanski et al. |
| 5,095,113 A | 3/1992 | Chiang |
| 5,922,648 A * | 7/1999 | Lorenz et al. .............. 504/233 |
| 6,239,071 B1 * | 5/2001 | Giencke et al. ............ 544/208 |

FOREIGN PATENT DOCUMENTS

| | | |
|---|---|---|
| AT | 97/47791 | 3/1999 |
| AU | 47790/97 | 3/1999 |
| BE | 612529 | 1/1962 |
| DE | 195 22 137 | 1/1997 |
| DE | 195 31 084 | 4/1998 |
| DE | 196 41 691 | 4/1998 |
| DE | 196 41 694 | 4/1998 |
| EP | 130 939 | 1/1985 |
| WO | WO 97/00254 | 1/1997 |
| WO | WO 97/08156 | 3/1997 |
| WO | WO-97/08156 * | 3/1997 |
| WO | WO-98/15537 A1 * | 4/1998 |

OTHER PUBLICATIONS

Shapiro et al., J. Amer. Chem. Soc. 81:3728–3736, 1958.*
J. of Am. Chem. Soc., vol. 81, (1859), pp. 3728–3736.
Chemical Abstract No. 6466A and corresponding CA service documents.
Chemical Abstract No. 9872D and corresponding CA service documents.
Angew Chem. Int. Ed. vol. 38, No. 8, 1999.
Database Crossfire (Chem. Berichte).
Database Crossfire (Arzneim. Forsch).
J. of Am. Chem. Soc., vol. 79, (1957), pp. 5064–5071.
Shapiro et al., J. of Amer. Chem. Soc. 81: 3728–3736, 1958.
Ghosh, P., et al. "1,2–Diphenylethy;amines as Potenial Non–stimulant Anorectics," Arzneim–Forsch/Drug Res., (1978) 28 (II) 1561–1564.

* cited by examiner

*Primary Examiner*—Venkataraman Balasubramanian
(74) *Attorney, Agent, or Firm*—Frommer Lawrence & Haug LLP

(57) ABSTRACT

The invention is in the technical field of the crop protection agents, such as herbicides and plant growth regulators, in particular of the herbicides for the selective control of harmful plants in crops of useful plants.

21 Claims, No Drawings

2,4-DIAMINO-1,3,5-TRIAZINES, THEIR PREPARATION, AND THEIR USE AS HERBICIDES AND PLANT GROWTH REGULATORS

The present application is a continuation of application Ser. No. 10/024,425 filed Dec. 18, 2001, now abandoned, which is a continuation of application Ser. No. 09/332,222 filed Jun. 14, 1999, now abandoned.

The invention is in the technical field of the crop protection agents, such as herbicides and plant growth regulators, in particular of the herbicides for the selective control of harmful plants in crops of useful plants.

It is known that 2-amino-4-(N-phenylalkylamino)-1,3,5-triazines which are substituted in the 6-position and which may be further substituted have herbicidal and plant-growth-regulating properties; cf. WO97/08156 and the literature cited therein, and WO98/15537 and the literature cited therein; cf. also aspects of WO97/00254 and the literature cited therein.

When the known active substances are used, some of them have disadvantages, be it an insufficient herbicidal action against harmful plants, too narrow a spectrum of harmful plants which can be controlled by an active substance, or too little selectivity in crops of useful plants. Other active substances cannot be produced economically on an industrial scale because their precursors and reagents are difficult to obtain, or their chemical stability properties are insufficient.

It is an object of the invention to provide alternative active substances of the type of the 2,4-diamino-1,3,5-triazines which, if appropriate, can be employed advantageously as herbicides or plant growth regulators.

The present invention relates to compounds of the formula (I) and salts thereof

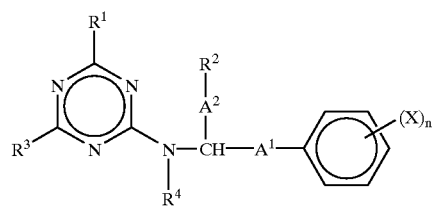

(I)

in which $R^1$ is aryl which is unsubstituted or substituted and, inclusive of substituents, preferably has 6 to 30 carbon atoms, or is $(C_3-C_9)$cycloalkyl which is unsubstituted or substituted and which, inclusive of substituents, preferably has 3 to 30 carbon atoms, or is heterocyclyl which is substituted or unsubstituted and which, inclusive of substituents, preferably has 2 to 30 carbon atoms, or $(C_1-C_6)$alkyl, $(C_2-C_6)$alkenyl or $(C_2-C_6)$alkynyl, each of the last-mentioned 3 radicals being unsubstituted or substituted by one or more radicals selected from the group consisting of halogen, hydroxyl, cyano, nitro, thiocyanato, $(C_2-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl and $(C_3-C_9)$cycloalkyl which is unsubstituted or substituted, and phenyl which is unsubstituted or substituted, and heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"— in which R', R" and R'" in each case independently of one another are $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, each of the 5 last-mentioned radicals being unsubstituted or substituted, and in which Z and Z' independently of one another are in each case an oxygen or sulfur atom, and which, inclusive of substituents, preferably has 1 to 30 carbon atoms, $R^2$ is $(C_3-C_9)$cycloalkyl which is unsubstituted or substituted, $(C_4-C_9)$cycloalkenyl which is unsubstituted or substituted, heterocyclyl which is unsubstituted or substituted, or phenyl, which is unsubstituted or substituted, $R^2$, inclusive of substituents, preferably having up to 30 carbon atoms, or $R^3$ is hydrogen, $(C_1-C_6)$alkyl, aryl or $(C_3-C_9)$cycloalkyl, each of the last-mentioned 3 radicals being unsubstituted or substituted, or a radical of the formula —N($B^1$-$D^1$)($B^2$-$D^2$) or —NR'—N($B^1$-$D^1$)($B^2$-$D^2$) in which $B^1$, $B^2$, $D^1$ and $D^2$ are in each case as defined below and R'=hydrogen, $(C_1-C_6)$alkyl or [$(C_1-C_4)$alkyl]carbonyl, $R^3$, inclusive of substituents, preferably having up to 20 carbon atoms, $R^4$ is a radical of the formula -$B^3$-$D^3$, $B^3$ and $D^3$ being as defined below and $R^4$, inclusive of substituents, preferably having up to 20 carbon atoms, $A^1$ is straight-chain alkylene having 1 to 5 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^4$-$D^4$, $B^4$ and $D^4$ being as defined below, $A^2$ is a direct bond or straight-chain alkylene having 1 to 4 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^5$-$D^5$ or a divalent radical of the formula $V^1$, $V^2$, $V^3$, $V^4$ or $V^5$,

—$CR^6R^7$—W*—$CR^8R^9$— (V¹)

—$CR^{10}R^{11}$—W*—$CR^{12}R^{13}$—$CR^{14}R^{15}$— (V²)

—$CR^{16}R^{17}$—$CR^{18}R^{19}$—W*—$CR^{20}R^{21}$— (V³)

—$CR^{22}R^{23}$—$CR^{24}R^{25}$—W*— (V⁴)

—$CR^{26}R^{27}$—W*— (V⁵)

each of the radicals $R^6$ to $R^{27}$ in each case independently of one another being hydrogen, halogen, nitro, cyano, thiocyanato or a radical of the formula -$B^6$-$D^6$, W* is in each case an oxygen atom, a sulfur atom or a group of the formula N($B^7$-$D^7$) and $B^5$, $B^6$, $B^7$, $D^5$, $D^6$ and $D^7$ are as defined below, $B^1$, $B^2$, $B^3$ and $B^7$ in each case independently of one another are a direct bond or a divalent group of the formulae —C(=Z*)—, —C(=Z*)—Z**—, —C(=Z*)—NH— or —C(=Z*)—NR*—, Z* being an oxygen or sulfur atom, Z** an oxygen or sulfur atom and R* $(C_1-C_6)$alkyl, aryl, aryl-$(C_1-C_6)$alkyl, $(C_3-C_9)$cycloalkyl or $(C_3-C_9)$ cycloalkyl-$(C_1-C_6)$alkyl, each of the 5 last-mentioned radicals being unsubstituted or substituted and, inclusive of the substituents, preferably having up to 20 carbon atoms, $B^4$, $B^5$ and $B^6$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —NR°—, —O—NR°—, NR°—O—, —NR°—CO—, —CO—NR°—, —O—CO—NR°— or —NR°—CO—O—, p being the integer 0, 1 or 2 and R° being hydrogen, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, each of the 5 last-mentioned radicals being unsubstituted or substituted and, inclusive of substituents, preferably having up to 20 carbon atoms, $D^1$, $D^2$, $D^3$, $D^4$, $D^5$ and $D^6$ in each case independently of one another are hydrogen, $(C_1-C_6)$alkyl, aryl, aryl-$(C_1-C_6)$alkyl, $(C_3-C_9)$cycloalkyl or $(C_3-C_9)$cycloalkyl-$(C_1-C_6)$alkyl, each of the 5 last-mentioned radicals being unsubstituted or substituted and, inclusive of substituents, preferably having up to 20 carbon atoms, or in each case two radicals $D^5$ of two groups -$B^5$-$D^5$ which are bonded to a carbon atom are linked to each other and form an alkylene group having 2 to 4 carbon atoms, this alkylene group being unsubstituted or substituted by one or more radicals selected from the group consisting of $(C_1-C_4)$alkyl and $(C_1-C_4)$alkoxy, $(X)_n$ is n substituents X, where the X in each case independently of one another are halogen, hydroxyl, amino, nitro, formyl, carboxyl, cyano, thiocyanato, aminocarbonyl or $(C_1-C_6)$alkyl, $(C_1-C_6)$alkoxy, $(C_1-C_6)$alkylthio, mono $(C_1-C_6)$alkylamino, di$(C_1-C_4)$alkylamino, $(C_2-C_6)$alkenyl, $(C_2-C_6)$alkynyl, [$(C_1-C_6)$alkyl]carbonyl, [$(C_1-C_6)$alkoxy]carbonyl, mono$(C_1-C_6)$alkylaminocarbonyl, di$(C_1-C_4)$alkylaminocarbonyl, N—$(C_1-C_6)$alkanoylamino or N—$(C_1-C_4)$alkanoyl-N—$(C_1-C_4)$alkylamino, each of the last-mentioned 13 radicals being unsubstituted or substituted, preferably unsubstituted or substituted by one or more radicals selected from the group consisting of halogen, hydroxyl, amino, nitro, formyl, carboxyl, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $(C_3-C_9)$cycloalkyl-amino, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, each of the last-mentioned 8 radicals being unsubstituted or having one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl and $(C_1-C_4)$alkoxycarbonyl, or is $(C_3-C_9)$cycloalkyl, $(C_3-C_9)$cycloalkoxy, $(C_3-C_9)$cycloalkylamino, phenyl, phenoxy, phenylthio, phenylcarbonyl, heterocyclyl, heterocyclyloxy, heterocyclylthio or heterocyclylamino, each of the last-mentioned 11 radicals being unsubstituted or substituted, preferably unsubstituted or substituted by one or more radicals selected from the group consisting of halogen, hydroxyl, amino, nitro, formyl, carboxyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono $(C_1-C_4)$alkylaminocarbonyl and di$(C_1-C_4)$ alkylaminocarbonyl, or two adjacent radicals X together are a fused cycle which has 4 to 6 ring atoms and is carbocyclic or which contains hetero ring atoms selected from the group consisting of O, S and N and which is unsubstituted or substituted by one or more radicals selected from the group consisting of halogen, $(C_1-C_4)$alkyl and oxo, n is 0, 1, 3, 4 or 5, preferably 0, 1, 2, 3 or 4, in particular 1 or 2, and heterocyclyl in the abovementioned radicals independently of one another is in each case a heterocyclic radical having 3 to 7 ring atoms and 1 to 3 hetero atoms selected from the group consisting of N, O and S, where a) the total of the carbon atoms in the radicals $A^1$ and $A^2$—$R^2$ amounts to at least 6 carbon atoms or b) the total of the carbon atoms in the radicals $A^1$ and $A^2$—$R^2$ amounts to 5 carbon atoms and $A^1$ is a group of the formula —CH$_2$— or —CH$_2$CH$_2$— and $R^1$ is $(C_1-C_4)$ alkyl, $(C_1-C_4)$haloalkyl, $(C_2-C_6)$haloalkenyl or $(C_3-C_9)$ cycloalkyl which is unsubstituted or substituted.

Unless specified in greater details, divalent radicals, for example, $B^1$=—C(=Z*)—Z**—, are defined such that, in the composite groups, for example -$B^1$-$D^1$, that bond of the divalent radical is linked to the group $D^1$ which appears on the right-hand side in the formula for the divalent radical, i.e. -$B^1$-$D^1$ is a group of the formula —C(=Z*)—Z** -$D^1$; a similar definition applies to analogous divalent radicals.

The compounds of the formula (I) can form salts when a basic group such as, for example, amino or alkylamino undergoes an addition reaction with a suitable inorganic or organic acid, such as, for example, HCl, HBr, $H_2SO_4$ or $HNO_3$, but also oxalic acid or sulfonic acids. Suitable substituents which are present in deprotonated form such as, for example, sulfonic acids or carboxylic acids, can form internal salts with those groups which are capable of undergoing protonation themselves, such as amino groups. Also, salts can be formed by replacing, in the case of suitable substituents such as, for example, sulfonic acids or carboxylic acids, the hydrogen by an agriculturally suitable cation. Examples of such salts are metal salts, in particular alkali metal salts or alkaline earth metal salts, in particular sodium salts and potassium salts, or else ammonium salts, salts with organic amines, or quaternary ammonium salts.

In formula (I) and in all subsequent formulae, the radicals alkyl, alkoxy, haloalkyl, haloalkoxy, alkylamino and alkylthio and the corresponding unsaturated and/or substituted radicals may be straight-chain or branched in the carbon skeleton in each case. Unless otherwise specified, the lower carbon skeletons, for example those having 1 to 6 carbon atoms, or in the case of unsaturated groups, those having 2 to 6 carbon atoms, are preferred for these radicals. Alkyl radicals, also in the composite meanings such as alkoxy, haloalkyl and the like, are, for example methyl, ethyl, n- or i-propyl, n-, i-, t- or 2-butyl, pentyls, hexyls, such as n-hexyl, i-hexyl and 1,3-dimethylbutyl, heptyls such as n-heptyl, 1-methylhexyl and 1,4-dimethylpentyl; alkenyl and alkynyl radicals have the meanings of the unsaturated radicals which are possible and which correspond to the alkyl radicals; for example, alkenyl is allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yl-1-yl, but-3-yl-1-yl, 1-methylbut-3-yl-1-yl.

Cycloalkyl is a carbocyclic saturated ring system having preferably 3–8 carbon atoms, for example cyclopropyl, cyclobutyl, cyclopentyl or cyclohexyl. Substituted cycloalkyl encompasses cyclic systems with substituents, the substituents being bonded to the cycloalkyl radical via a double bond, for example an alkylidene group such as methylidene. Substituted cycloalkyl also encompasses polycyclic aliphatic systems such as, for example, bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, adamantan-1-yl and adamantan-2-yl.

Cycloalkenyl is a carbocyclic non-aromatic partially unsaturated ring system having preferably 4–8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. The explanations given for substituted cycloalkyl apply analogously to substituted cycloalkenyl.

Halogen is, for example, fluorine, chlorine, bromine or iodine. Haloalkyl, -alkenyl and -alkynyl are alkyl, alkenyl or alkynyl which are partially or fully substituted by halogen, preferably by fluorine, chlorine and/or bromine, in particular by fluorine or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies analogously to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and similar, preferably phenyl.

A heterocyclic radical or ring (heterocyclyl) can be saturated, unsaturated or heteroaromatic; it preferably contains one or more, in particular 1, 2 or 3, hetero atoms in the heterocyclic ring, preferably selected from the group consisting of nitrogen, oxygen and sulfur; it is preferably an aliphatic heterocyclyl radical having 3 to 7 ring atoms or a heteroaromatic radical having 5 or 6 ring atoms. The heterocyclic radical can be, for example, a heteroaromatic radical or ring (heteroaryl) such as, for example, a mono-, bi- or polycyclic aromatic system in which at least one ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, or it is a partially or fully hydrogenated radical such as oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl. Suitable substituents for a substituted heterocyclic radical are those mentioned further below, and in addition also oxo. The oxo group may also occur on those hetero ring atoms which can exist at various oxidation stages, for example in the case of nitrogen and sulfur.

Substituted radicals such as a substituted alkyl, alkenyl, alkynyl, aryl, phenyl, benzyl, heterocyclyl and heteroaryl radical are, for example, a substituted radical which is derived from the unsubstituted skeleton, the substituents having, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl; the term "substituted radicals" such as substituted alkyl and the like include, in addition to the abovementioned saturated hydrocarbon-containing radicals, corresponding unsaturated aliphatic and aromatic radicals as substituents, such as optionally substituted alkenyl, alkynyl, alkenyloxy, alkynyloxy, phenyl, phenoxy and the like. In the case of substituted cyclic radicals with aliphatic moieties in the ring, the definition also encompasses cyclic systems with those substituents which are bonded to the ring by means of a double bond, for example by means of an alkylidene group such as methylidene or ethylidene.

In the case of radicals which have carbon atoms, those having 1 to 4 carbon atoms, in particular 1 or 2 carbon atoms, are preferred. Preferred substituents are, as a rule, those selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano.

Especially preferred are the substituents methyl, methoxy and chlorine.

Mono- or disubstituted amino is a chemically stable radical selected from the group consisting of substituted amino radicals which are n-substituted, for example, by one, or two, identical or different radicals selected from the group consisting of alkyl, alkoxy, acyl and aryl; preferably monoalkylamino, dialkylamino, acylamino, arylamino, N-alkyl-N-arylamino and N-heterocycles; alkyl radicals having 1 to 4 carbon atoms are preferred; aryl is preferably phenyl or substituted phenyl; acyl is covered by the definition given further below, preferably $(C_1-C_4)$alkanoyl. This applies analogously to substituted hydroxylamino or hydrazino.

Optionally substituted phenyl is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid and radicals of acids derived therefrom, such as thiocarboxylic acid, optionally n-substituted iminocarboxylic acids or the radical of carbonic monoesters, optionally n-substituted carbamic acid, sulfonic acids, sulfinic acids, phosphonic acids, phosphinic acids. Acyl is, for example, formyl, alkylcarbonyl such as [$(C_1-C_4)$alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals may be further substituted in each case in the alkyl or phenyl moiety, for example in the alkyl moiety by one or more radicals selected from the group consisting of halogen, alkoxy, phenyl and phenoxy; examples of substituents in the phenyl moiety are those substituents which have already been mentioned further above in general terms for substituted phenyl.

The invention furthermore relates to all stereoisomers encompassed by formula (I) and mixtures of these. Such compounds of the formula (I) contain one or more asymmetric carbon atoms or else double bonds, which are not indicated specifically in the formulae (I). The formula (I)

encompasses all stereoisomers which are possible and which are defined by their specific spatial form, such as enantiomers, diastereomers, Z- and E-isomers, and they can be obtained from stereoisomer mixtures by customary methods or else prepared by means of stereoselective reactions in combination with the use of stereochemically pure starting materials.

Compounds of the abovementioned formula (I) according to the invention or their salts which are of particular interest, mainly because of their more potent herbicidal action, better selectivity and/or because they are easier to prepare are those in which individual radicals have one of the preferred meanings which have already been mentioned above or are mentioned hereinbelow, or in particular those in which one or more of the preferred meanings which have already been mentioned or which are mentioned hereinbelow are combined with each other.

$R^1$ is preferably phenyl which is unsubstituted or substituted by one or more radicals selected from the group consisting of halogen, hydroxyl, amino, nitro, formyl, carboxyl, sulfo, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylamino-carbonyl, $(C_1-C_4)$alkylsulfonyl and $(C_1-C_4)$haloalkylsulfonyl and which, inclusive of substituents, has 6 to 30 carbon atoms, preferably 6 to 20 carbon atoms, in particular 6 to 15 carbon atoms.

$R^1$ is preferably also $(C_3-C_9)$cycloalkyl which is unsubstituted or substituted by one or more radicals selected from the group consisting of halogen, hydroxyl, amino, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino and which, inclusive of substituents, has 3 to 30 carbon atoms, preferably 3 to 20 carbon atoms, in particular 3 to 15 carbon atoms.

$R^1$ is preferably also heterocyclyl which is unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl and which, inclusive of substituents, has 2 to 30 carbon atoms, preferably 2 to 20 carbon atoms, in particular 2 to 15 carbon atoms.

Here and also in other radicals, heterocycyl is preferably a heterocyclic radical having 3 to 7, in particular 3 to 6, ring atoms and a hetero atom selected from the group consisting of N, O and S, for example pyridyl, thienyl, furyl, pyrrolyl, oxiranyl, oxetanyl, oxolanyl (=tetrahydrofuryl), oxanyl, pyrrolidyl, piperidyl, or is a heterocyclic radical having two or three hetero atoms selected from the group consisting of pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl, morpholinyl.

$R^1$ is preferably also $(C_1-C_6)$alkyl, $(C_2-C_6)$alkenyl or $(C_2-C_6)$alkynyl, each of the last-mentioned 3 radicals being unsubstituted or substituted by one or more radicals selected from the group consisting of halogen, hydroxyl, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl and $(C_3-C_6)$cycloalkyl which is unsubstituted or substituted by one or more radicals selected from the group consisting of halogen, hydroxyl, amino, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino, and phenyl and heterocyclyl, each of the two last-mentioned radicals being unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"— in which R', R" and R'" in each case independently of one another are $(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, each of the 5 last-mentioned radicals being unsubstituted or substituted by one or more radicals selected from the group consisting of halogen, hydroxyl, amino, nitro, formyl, cyano, thiocyanato, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, $(C_3-C_6)$cycloalkyl and in the case of cyclic radicals also $(C_1-C_4)$alkyl and $(C_1-C_4)$haloalkyl, and in which Z and Z' independently of one another are in each case an oxygen or sulfur atom, and which, inclusive of substituents, preferably has 1 to 20 carbon atoms, in particular 1 to 15 carbon atoms, $R^1$ is preferably $(C_1-C_4)$alkyl which is unsubstituted or substituted by one or more radicals selected from the group consisting of halogen $(C_1-C_4)$alkoxy, $(C_1-C_4)$alkylthio, $(C_1-C_4)$alkylsulfonyl, $(C_3-C_9)$cycloalkyl which is unsubstituted or substituted, and phenyl which is unsubstituted or substituted by one or more radicals selected from the group consisting of halogen, $(C_1-C_4)$alkyl and $(C_1-C_4)$haloalkyl, $(C_1-C_4)$alkoxy, $(C_1-C_4)$haloalkoxy, $(C_1-C_4)$alkylthio, amino, mono- and di[$(C_1-C_4)$alkyl]amino, $(C_1-C_4)$alkanoylamino, benzoylamino, nitro, cyano, [$(C_1-C_4)$alkyl]carbonyl, formyl, carbamoyl, mono- and di[$(C_1-C_4)$alkyl]aminocarbonyl and $(C_1-C_4)$alkylsulfonyl and heterocycly having 3 to 6 ring atoms and 1 to 3 hetero ring atoms selected from the group consisting of nitrogen, oxygen and sulfur, the ring being unsubstituted or substituted by one or more radicals selected from the group consisting of halogen, $(C_1-C_4)$alkyl and oxo, or phenyl which is unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$ alkylaminocarbonyl, di($C_1$–$C_4$)alkylamino-carbonyl, ($C_1$–$C_4$)alkylsulfonyl and ($C_1$–$C_4$)haloalkylsulfonyl and which, inclusive of substituents, has 2 to 30 carbon atoms, preferably 2 to 20 carbon atoms, in particular 2 to 15 carbon atoms.

$R^1$ is furthermore by way of preference ($C_1$–$C_4$)alkyl, ($C_1$–$C_4$)haloalkyl, benzyl or [($C_3$–$C_6$)cycloalkyl]-($C_1$–$C_2$)alkyl, in particular ($C_1$–$C_4$)alkyl, ($C_1$–$C_4$) haloalkyl or [($C_3$–$C_6$)cycloalkyl]methyl, preferably —$CH_3$, —$CH_2F$, —$CHF_2$, —$CF_3$, —$CH_2Cl$, —$CHCl_2$, —$CCl_3$, —$CH_2Br$, —$CHBr_2$, —$CH_2CH_3$, —$CH_2CH_2F$, —$CF_2CHF_2$, —$CH_2CH_2Cl$, —$CH_2CH_2Br$ —$CH(CH_3)_2$, —$CF(CH_3)_2$, —$C(CH_3)_2Cl$, —$CH_2CH_2CH_2F$, —$CH_2CH_2CH_2Cl$ or cyclopropylmethyl.

The following meanings of $R^2$ are of particular interest, independently of the radicals $R^1$, $R^3$, $R^4$, $A^1$, $A^2$ and $(X)_n$ and preferably in combination with preferred meanings of one or more of these radicals:

$R^2$ is preferably ($C_3$–$C_9$)cycloalkyl which is unsubstituted or substituted by one or more radicals selected from the group consisting of the radicals A), B), C) and D), where Group A) is composed of the radicals halogen, hydroxyl, amino, nitro, formyl, carboxyl, aminocarbonyl, sulfo, cyano, thiocyanato and oxo, Group B) is composed of the radicals ($C_1$–$C_6$)alkyl, ($C_1$–$C_6$)alkoxy, ($C_1$–$C_6$)alkylthio, mono($C_1$–$C_6$) alkylamino, di($C_1$–$C_4$)alkylamino, ($C_2$–$C_6$)alkenyl, ($C_2$–$C_6$)alkynyl, ($C_3$–$C_9$)cycloalkyl, ($C_4$–$C_9$) cycloalkenyl, ($C_1$–$C_6$)alkylidene, ($C_4$–$C_9$) cycloalkylidene, radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"'— and R'R"N—C(=Z')—NR"'— where R', R" and R"' in each case independently of one another are ($C_1$–$C_6$) alkyl, phenyl, phenyl-($C_1$–$C_6$)alkyl, ($C_3$–$C_9$)cycloalkyl or ($C_3$–$C_9$)cycloalkyl-($C_1$–$C_6$)alkyl and where Z and Z' independently of one another are in each case an oxygen or sulfur atom, Group C) is composed of radicals as shown for group B), but each radical being substituted by one or more radicals selected from the group consisting of halogen, hydroxyl, amino, nitro, formyl, carboxyl, sulfo, cyano, thiocyanato, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$) alkylamino, di($C_1$–$C_4$)alkylamino, ($C_3$–$C_9$)cycloalkyl, ($C_4$–$C_9$)cycloalkylene, ($C_4$–$C_9$)cycloalkylidene, [($C_1$–$C_4$)alkyl]carbonyl, [($C_1$–$C_4$)alkoxy]carbonyl, aminocarbonyl, mono($C_1$–$C_4$)alkylaminocarbonyl, di($C_1$–$C_4$)alkylaminocarbonyl, phenyl, phenoxy, phenylthio, phenylcarbonyl, heterocyclyl, heterocyclyloxy, heterocyclylthio and heterocyclylamino, each of the last-mentioned 21 radicals being unsubstituted or substituted by one or more radicals selected from the group consisting of halogen, nitro, cyano, ($C_1$–$C_4$)alkoxy, ($C_1$–$C_4$)alkylthio, ($C_1$–$C_4$) haloalkoxy, formyl, ($C_1$–$C_4$)alkylcarbonyl and ($C_1$–$C_4$)alkoxycarbonyl and, in the case of cyclic radicals, also ($C_1$–$C_4$)alkyl, ($C_1$–$C_4$)haloalkyl and ($C_1$–$C_6$)alkylidene, and in the case of cyclic radicals also ($C_1$–$C_6$)alkyl, ($C_1$–$C_6$)haloalkyl and ($C_1$–$C_6$) alkylidene, and Group D) is composed of divalent or trivalent aliphatic bridges having 1 to 6, preferably 1 to 4, carbon atoms which, in the case of divalent bridges, connect two and in the case of trivalent bridges three carbon atoms of the cyclic skeleton and the radical $R^2$ thus represents the radical of a bicycle or tricycle, each of the bridges being unsubstituted or substituted by one or more substituents selected from the group consisting of halogen, nitro, cyano, ($C_1$–$C_4$)alkyl, ($C_1$–$C_4$)alkoxy, ($C_1$–$C_4$)alkylthio, ($C_1$–$C_4$)haloalkyl, ($C_1$–$C_4$) haloalkoxy, formyl, ($C_1$–$C_4$)alkylcarbonyl, ($C_1$–$C_4$) alkoxycarbonyl and oxo, and where $R^2$, inclusive of substituents, preferably has 3 to 20 carbon atoms, in particular 3 to 15 carbon atoms. Preferred ($C_3$–$C_9$)cycloalkyl radicals are cyclopropyl, cyclobutyl, cyclopentyl or cyclohexyl, in particular cyclopropyl, cyclobutyl or cyclopentyl.

$R^2$ is preferably also ($C_4$–$C_9$)cycloalkenyl which is unsubstituted or substituted by one or more radicals selected from the group consisting of the radicals A), B), C) and D) as they are defined as radicals for $R^2$=($C_3$–$C_9$)cycloalkyl, and, inclusive of substituents, preferably has 4 to 20 carbon atoms, in particular 4 to 15 carbon atoms.

Preferred as ($C_4$–$C_9$)cycloalkenyl radicals are 1-cyclobutenyl, 2-cyclobutenyl, 1-cyclopentenyl, 2-cyclopentenyl and 3-cyclopentenyl.

$R^2$ is preferably also heterocyclyl which is unsubstituted or substituted by one or more radicals selected from the group consisting of the radicals A), B), C) and D) as they are defined as radicals for $R^2$=($C_3$–$C_9$)cycloalkyl.

Heterocyclyl in this context is preferably a heterocyclic radical having 3 to 6 from amongst the group consisting of pyridyl, thienyl, furyl, pyrrolyl, oxiranyl, 2-oxetanyl, 3-oxetanyl, oxolanyl (=tetrahydrofuryl), pyrrolidyl, piperidyl, in particular oxiranyl, 2-oxetanyl, 3-oxetanyl or oxolanyl, or is a heterocyclic radical having two or three hetero atoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

$R^2$ is preferably also phenyl which is unsubstituted or substituted by one or more radicals selected from the group consisting of the radicals A), B) and C) as they are defined as radicals for $R^2$=($C_3$–$C_9$)cycloalkyl.

$R^2$, inclusive of substituents, preferably has up to 20 carbon atoms, in particular up to 15 carbon atoms, very especially up to 10 carbon atoms.

$R^2$ is preferably ($C_3$–$C_9$)cycloalkyl which is unsubstituted or substituted by one or more radicals selected from the group consisting of the radicals A), B), C) and D), where Group A) is composed of the radicals halogen, hydroxyl, nitro, formyl, aminocarbonyl, cyano and thiocyanato, Group B) is composed of the radicals ($C_1$–$C_4$)alkyl, ($C_1$–$C_4$)alkoxy, ($C_1$–$C_4$)alkylthio, mono($C_1$–$C_4$) alkylamino, di($C_1$–$C_4$)alkylamino, ($C_2$–$C_4$)alkenyl, ($C_2$–$C_4$)alkynyl, ($C_3$–$C_6$)cycloalkyl, ($C_4$–$C_6$) cycloalkenyl, ($C_1$–$C_4$)alkylidene, ($C_4$–$C_6$) cycloalkylidene, radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"'— and R'R"N—C(=Z')—NR"'— where R', R" and R"' in each case independently of one another are ($C_1$–$C_4$) alkyl, phenyl, phenyl-($C_1$–$C_4$)alkyl, ($C_3$–$C_6$)cycloalkyl or ($C_3$–$C_6$)cycloalkyl-($C_1$–$C_6$)alkyl and where Z and Z' independently of one another are in each case an oxygen or sulfur atom, Group C) is composed of radicals as shown in Group B), but each radical is substituted by one or more radicals selected from the group consisting of halogen, ($C_1$–$C_4$)

alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, where each of the last-mentioned 8 radicals is unsubstituted or has one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, $(C_1-C_4)$alkylcarbonyl and $(C_1-C_4)$alkoxycarbonyl, and Group D) is composed of divalent aliphatic bridges which connect two carbon atoms of the cyclic skeleton, the radical $R^2$ thus representing the radical of a bicycle, for example bicyclo[1.1.0]butan-1-yl, bicyclo[1.1.0]butan-2-yl, bicyclo[2.1.0]pentan-1-yl, bicyclo[2.1.0]pentan-2-yl or bicyclo[2.1.0]pentan-5-yl, where each of the bridges is unsubstituted or substituted by one or more substituents selected from the group consisting of halogen, $(C_1-C_4)$alkyl, $(C_1-C_4)$alkoxy, $(C_1-C_4)$alkylthio, $(C_1-C_4)$haloalkyl, $(C_1-C_4)$haloalkoxy, $(C_1-C_4)$alkyl-carbonyl, $(C_1-C_4)$alkoxycarbonyl and oxo.

$R^2$ is especially preferably $(C_3-C_9)$cycloalkyl which is unsubstituted or substituted by one or more radicals selected from the group consisting of halogen, hydroxyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, $(C_1-C_4)$alkylidene, mono$(C_1-C_4)$alkylamino and di$(C_1-C_4)$alkylamino or heterocyclyl or phenyl, each of the last-mentioned two radicals being unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, heterocyclyl having 3 to 6 ring atoms, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl and $(C_1-C_4)$haloalkylsulfonyl.

The following meanings of $R^3$ are of particular interest, independently of the radicals $R^1$, $R^2$, $R^4$, $A^1$, $A^2$ and $(X)_n$ and preferably in combination with preferred meanings of one or more of these radicals:

$R^3$ is hydrogen, $(C_1-C_4)$alkyl which is unsubstituted or substituted by one or more radicals selected from the group consisting of halogen, hydroxyl, amino, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino, or phenyl or $(C_3-C_6)$cycloalkyl, each of the last-mentioned 2 radicals being unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylamino-carbonyl, di$(C_1-C_4)$alkylaminocarbonyl, $(C_1-C_4)$alkylsulfonyl and $(C_1-C_4)$haloalkylsulfonyl, or a radical of the formula N($B^1$-$D^1$)($B^2$-$D^2$) where $B^1$, $B^2$, $D^1$ and $D^2$ are as already defined or preferably as defined further below, in particular amino.

The following meanings of $R^4$ are of particular interest, independently of the radicals $R^1$ to $R^3$, $A^1$, $A^2$ and $(X)_n$ and preferably in combination with preferred meanings of one or more of these radicals:

$R^4$ is a radical of the formula -$B^3$-$D^3$ where $B^3$ and $D^3$ are preferably as defined further below, $R^4$ is preferably hydrogen, $(C_1-C_4)$alkyl, phenyl or $(C_3-C_6)$cycloalkyl, each of the 3 last-mentioned radicals being unsubstituted or substituted by one or more radicals selected from the group consisting of halogen, hydroxyl, amino, nitro, formyl, carboxyl, sulfonyl, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and in the case of cyclic radicals also $(C_1-C_4)$alkyl and $(C_1-C_4)$haloalkyl, or formyl, [$(C_1-C_4)$alkyl]carbonyl, [$(C_1-C_4)$alkoxy]carbonyl, aminocarbonyl, mono$(C_1-C_4)$alkylaminocarbonyl or di$(C_1-C_4)$alkylaminocarbonyl; in particular hydrogen, methyl, ethyl, n-propyl or isopropyl; especially preferably hydrogen.

The following meanings of $A^1$ are of particular interest, independently of the radicals $R^1$ to $R^4$, $A^2$ and $(X)_n$ and preferably in combination with preferred meanings of one or more of these radicals:

$A^1$ is straight-chain alkylene having 1 to 5 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and a radical of the formula -$B^4$-$D^4$, $B^4$ is a direct bond or a divalent group of the formulae —O—, —SO$_2$—, —CO—, —O—CO—, —NR$^o$—, —NR$^o$—CO—, —CO—NR$^o$—, —O—CO—NR$^o$— or —NR$^o$—CO—O—, where $R^o$ and $D^4$ independently of one another are in each case hydrogen, $(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, each of the last-mentioned 5 radicals being unsubstituted or substituted by one or more radicals selected from the group consisting of halogen, hydroxyl, amino, nitro, formyl, carboxyl, sulfonyl, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and in the case of cyclic radicals also $(C_1-C_4)$alkyl and $(C_1-C_4)$haloalkyl.

$A^1$ is preferably a radical of the formula —CH$_2$—, —CH$_2$CH$_2$—, —CH$_2$CH$_2$CH$_2$—, —CH$_2$CH$_2$CH$_2$CH$_2$ or —CH$_2$CH$_2$CH$_2$CH$_2$CH$_2$— which is unsubstituted. Also preferred is one of the above radicals which is substituted by one or else more than one of the abovementioned radicals -$B^4$-$D^4$. $A^1$ is especially preferably a radical of the formula —CH$_2$CH$_2$— or —CH$_2$CH$_2$CH$_2$— which is unsubstituted or substituted by one or two radicals of the formula hydroxyl, $(C_1-C_4)$alkyl or $(C_1-C_4)$alkoxy.

The following meanings of $A^2$ are of particular interest, independently of the radicals $R^1$ to $R^4$, $A^1$ and $(X)_n$ and preferably in combination with preferred meanings of one or more of these radicals:

$A^2$ is preferably a direct bond or a group of the formula —$CH_2$—, —$CH_2CH_2$—, —$CH_2CH_2CH_2$— or —$CH_2CH_2CH_2CH_2$—, each of the 4 last-mentioned divalent radicals being unsubstituted or substituted by one or more radicals selected from the group consisting of halogen, nitro, cyano, thiocyanato and radicals of the formula -$B^5$-$D^5$—, or a divalent radical of the formula $V^1$, $V^2$, $V^3$, $V^4$ or $V^5$,

—$CR^6R^7$—$W^*$—$CR^8R^9$— (V$^1$)

—$CR^{10}R^{11}$—$W^*$—$CR^{12}R^{13}$—$CR^{14}R^{15}$— (V$^2$)

—$CR^{16}R^{17}$—$CR^{18}R^{19}$—$W^*$—$CR^{20}R^{21}$— (V$^3$)

—$CR^{22}R^{23}$—$CR^{24}R^{25}$—$W^*$— (V$^4$)

—$CR^{26}R^{27}$—$W^*$— (V$^5$)

where each of the radicals $R^6$ to $R^{27}$ in each case independently of one another is hydrogen, halogen, nitro, cyano, thiocyanato or a radical of the formula -$B^6$-$D^6$, $W^*$ is in each case oxygen, sulfur or a group of the formula $N(B^7$-$D^7)$ and $B^5$, $B^6$, $B^7$, $D^5$, $D^6$ and $D^7$ are as defined below, $A^2$ is especially preferably a direct bond or a group of the formula —$CH_2$—, —$CH_2CH_2$—, —$CH_2CH_2CH_2$—, —$CH_2CH_2CH_2CH_2$—, —$CH_2$—O—$CH_2$—, —$CH_2$—O—$CH_2$—$CH_2$—, —$CH_2$—$CH_2$—O—$CH_2$—, —$CH_2$—S—$CH_2$—, —$CH_2$—S—$CH_2$—$CH_2$—, —$CH_2$—$CH_2$—S—$CH_2$—, —$CH_2$—NH—$CH_2$—, —$CH_2$—NH—$CH_2$—$CH_2$—, —$CH_2$—$CH_2$—NH—$CH_2$—, —$CH_2$—N(CH$_3$)—$CH_2$—, —$CH_2$—N(CH$_3$)—$CH_2$—$CH_2$— or —$CH_2$—$CH_2$—N(CH$_3$)—$CH_2$—.

$B^1$, $B^2$, $B^3$ and $B^7$ are preferably in each case independently of one another a direct bond or a divalent group of the formulae —C(=Z*)—, —C(=Z*)—Z**—, —C(=Z*)—NH— or —C(=Z*)—NR*— where Z*=oxygen or sulfur, Z**=oxygen or sulfur and R*=(C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, where each of the 5 last-mentioned radicals is unsubstituted or substituted, preferably unsubstituted or substituted by one or more radicals selected from the group consisting of halogen, hydroxyl, amino, nitro, formyl, carboxyl, sulfo, cyano, thiocyanato, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and in the case of cyclic radicals also (C$_1$–C$_4$)alkyl and (C$_1$–C$_4$)haloalkyl;

it is furthermore preferred for $B^1$, $B^2$, $B^3$ and $B^7$ independently of one another to be a direct bond or a divalent group of the formulae —C(=Z*)—, —C(=Z*)—Z**—, —C(=Z*)—NH— or —C(=Z*)—NR*—, where Z*=O or S, Z**=O or S and R*=(C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, where each of the 5 last-mentioned radicals is unsubstituted or substituted by one or more radicals selected from the group consisting of halogen, hydroxyl, amino, formyl, (C$_1$–C$_4$)alkoxy, (C$_1$–C$_4$)haloalkoxy, (C$_1$–C$_4$)alkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl and in the case of cyclic radicals also (C$_1$–C$_4$)alkyl and (C$_1$–C$_4$)haloalkyl, in particular R*=(C$_1$–C$_4$)alkyl or (C$_3$–C$_6$)cycloalkyl or in particular R*=phenyl or phenyl-(C$_1$–C$_4$)alkyl, where each of the two last-mentioned radicals is unsubstituted in the phenyl moiety or substituted by one or more radicals selected from the group consisting of halogen, (C$_1$–C$_4$)alkyl, (C$_1$–C$_4$)haloalkyl, (C$_1$–C$_4$)alkoxy or (C$_1$–C$_4$)haloalkoxy.

$B^4$, $B^5$ and $B^6$ are preferably in each case independently of one another a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —NR$^o$—, —O—NR$^o$—, —NR$^o$—O—, —NR$^o$—CO—, —CO—NR$^o$—, —O—CO—NR$^o$— or —NR$^o$—CO—O—, where p is the integer 0, 1 or 2 and R$^o$=hydrogen, (C$_1$–C$_4$)alkyl, phenyl, phenyl-(C$_1$–C$_4$)alkyl, (C$_3$–C$_6$)cycloalkyl or (C$_3$–C$_6$)cycloalkyl-(C$_1$–C$_4$)alkyl, each of the 5 last-mentioned radicals being unsubstituted or substituted by one or more radicals selected from the group consisting of halogen, hydroxyl, amino, nitro, formyl, carboxyl, sulfo, cyano, thiocyanato, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and in the case of cyclic radicals also (C$_1$–C$_4$)alkyl and (C$_1$–C$_4$)haloalkyl, and in particular R$^o$=hydrogen, (C$_1$–C$_4$)alkyl or (C$_3$–C$_6$)cycloalkyl or in particular R$^o$=phenyl or phenyl-(C$_1$–C$_4$)alkyl, each of the two last-mentioned radicals being unsubstituted in the phenyl moiety or substituted by one or more radicals selected from the group consisting of halogen, (C$_1$–C$_4$)alkyl, (C$_1$–C$_4$)haloalkyl, (C$_1$–C$_4$)alkoxy or (C$_1$–C$_4$)haloalkoxy.

It is furthermore preferred that $B^4$, $B^5$ and $B^6$ independently of one another are a direct bond or a divalent group of the formulae —O—, —S(O)$_p$—, —CO—, —O—CO—, —CO—O—, —S—CO—, —CO—S—, —NR$^o$—, —NR$^o$—CO—, —CO—NR$^o$—, —O—CO—NR$^o$— or —NR$^o$—CO—O—, p being the integer 0, 1 or 2, in particular 0 or 2, and R$^o$ having the abovementioned meaning, very especially H or (C$_1$–C$_4$)alkyl.

$D^1$, $D^2$, $D^3$, $D^4$, $D^5$ and $D^6$ independently of one another preferably are hydrogen, (C$_1$–C$_6$)alkyl, phenyl, phenyl-(C$_1$–C$_4$)alkyl, (C$_3$–C$_6$)cycloalkyl or (C$_3$–C$_6$)cycloalkyl-(C$_1$–C$_6$)alkyl, each of the 5 last-mentioned radicals being unsubstituted or substituted, preferably unsubstituted or substituted by one or more radicals selected from the group consisting of halogen, hydroxyl, amino, nitro, formyl, carboxyl, sulfo, cyano, thiocyanato, (C$_1$–C$_4$)alkoxy, (C$_1$–C$_4$)haloalkoxy, (C$_1$–C$_4$)alkylthio, (C$_1$–C$_4$)haloalkylthio, mono(C$_1$–C$_4$)alkylamino, di(C$_1$–C$_4$)alkylamino, (C$_3$–C$_9$)cycloalkyl, [(C$_1$–C$_4$)alkyl]carbonyl, [(C$_1$–C$_4$)alkoxy]carbonyl, aminocarbonyl, mono(C$_1$–C$_4$)alkylaminocarbonyl, di(C$_1$–C$_4$)alkylaminocarbonyl, (C$_1$–C$_4$)alkylsulfonyl, (C$_1$–C$_4$)haloalkylsulfonyl and in the case of cyclic radicals also (C$_1$–C$_4$)alkyl and (C$_1$–C$_4$)haloalkyl.

It is furthermore preferred that $D^1$, $D^2$, $D^3$, $D^4$, $D^5$ and $D^6$ independently of one another are (C$_1$–C$_4$)alkyl, phenyl, phenyl-(C$_1$–C$_4$)alkyl, (C$_3$–C$_6$)cycloalkyl or (C$_3$–C$_6$)

cycloalkyl-$(C_1-C_4)$alkyl, each of the 5 last-mentioned radicals being unsubstituted or substituted by one or more radicals selected from the group consisting of halogen, hydroxyl, amino, formyl, $(C_1-C_4)$alkoxy, $(C_1-C_4)$haloalkoxy, $(C_1-C_4)$alkylthio, mono$(C_1-C_4)$alkylamino, di$(C_1-C_4)$alkylamino, $(C_3-C_9)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl and in the case of cyclic radicals also $(C_1-C_4)$alkyl and $(C_1-C_4)$haloalkyl, and are, in particular, $(C_1-C_4)$alkyl or $(C_3-C_6)$cycloalkyl or phenyl or phenyl-$(C_1-C_4)$alkyl, each of the two last-mentioned radicals being unsubstituted in the phenyl moiety or substituted by one or more radicals selected from the group consisting of halogen, $(C_1-C_4)$alkyl, $(C_1-C_4)$haloalkyl, $(C_1-C_4)$alkoxy or $(C_1-C_4)$haloalkoxy.

The following meanings of $(X)_n$ are of particular interest, independently of the radicals $R^1$ to $R^4$, $A^1$ and $A^2$ and preferably in combination with preferred meanings of one or more of these radicals:

$(X)_n$ is n substituents X, where the X preferably in each case independently of one another are halogen, hydroxyl, amino, nitro, formyl, carboxyl, cyano, thiocyanato, aminocarbonyl or $(C_1-C_4)$alkyl, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, [$(C_1-C_4)$alkyl]carbonyl, [$(C_1-C_4)$alkoxy]carbonyl, mono$(C_1-C_4)$alkylaminocarbonyl, di$(C_1-C_4)$alkylaminocarbonyl, N—$(C_1-C_6)$alkanoylamino or N—$(C_1-C_4)$alkanoyl-N—$(C_1-C_4)$alkylamino, each of the last-mentioned 13 radicals being unsubstituted or substituted, preferably unsubstituted or substituted by one or more radicals selected from the group consisting of halogen, hydroxyl, amino, cyano, thiocyanato, $(C_1-C_4)$alkoxy, $(C_1-C_4)$haloalkoxy, $(C_1-C_4)$alkylthio, mono$(C_1-C_4)$alkylamino, di$(C_1-C_4)$alkylamino, $(C_3-C_6)$cycloalkyl, $(C_3-C_6)$cycloalkylamino, [$(C_1-C_4)$alkyl]carbonyl, [$(C_1-C_4)$alkoxy]carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, each of the last-mentioned 8 radicals being unsubstituted or having one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl and $(C_1-C_4)$alkoxycarbonyl, or $(C_3-C_9)$cycloalkyl, phenyl, phenoxy, phenylthio, phenylcarbonyl, heterocyclyl, heterocyclyloxy, heterocyclylthio or heterocyclylamino, each of the last-mentioned 9 radicals being unsubstituted or substituted, preferably unsubstituted or substituted by one or more radicals selected from the group consisting of halogen, hydroxyl, amino, nitro, formyl, carboxyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, [$(C_1-C_4)$alkyl]carbonyl, [$(C_1-C_4)$alkoxy]carbonyl, aminocarbonyl, mono$(C_1-C_4)$alkylaminocarbonyl and di$(C_1-C_4)$alkylaminocarbonyl, or two adjacent radicals X together are a fused cycle which has 4 to 6 ring atoms and is carbocyclic or contains hetero ring atoms selected from the group consisting of O, S and N and which is unsubstituted or substituted by one or more radicals selected from the group consisting of halogen, $(C_1-C_4)$alkyl and oxo.

n is preferably 0, 1, 2 or 3, in particular 1 or 2.

$(X)_n$ is preferably furthermore n substituents X, where the X in each case independently of one another are halogen, hydroxyl, amino, nitro, formyl, carboxyl, cyano, thiocyanato, $(C_1-C_4)$alkyl, cyano-$(C_1-C_4)$alkyl, $(C_1-C_4)$alkoxy, $(C_1-C_4)$alkylamino, di-[$(C_1-C_4)$alkyl]amino, halo-$(C_1-C_4)$alkyl, hydroxy-$(C_1-C_4)$alkyl, $(C_1-C_4)$alkoxy-$(C_1-C_4)$alkyl, halo$(C_1-C_4)$alkoxy-$(C_1-C_4)$alkyl, $(C_1-C_4)$alkylthio, halo-$(C_1-C_4)$alkylthio, $(C_2-C_6)$alkenyl, halo-$(C_2-C_6)$alkenyl, $(C_2-C_6)$alkynyl, halo-$(C_2-C_6)$alkynyl, $(C_1-C_4)$alkylamino-$(C_1-C_4)$alkyl, di-[$(C_1-C_4)$alkyl]-amino-$(C_1-C_4)$alkyl, $(C_3-C_6)$cycloalkylamino-$(C_1-C_4)$alkyl, $(C_3-C_9)$cycloalkyl, heterocyclyl-$(C_1-C_4)$alkyl having 3 to 9 ring members, the cyclic groups in the last-mentioned 3 radicals being unsubstituted or substituted by one or more radicals, preferably up to three radicals, selected from the group consisting of $(C_1-C_4)$alkyl, halogen and cyano, or phenyl, phenoxy, phenylcarbonyl, phenylcarbonyl-$(C_1-C_4)$alkyl, $(C_1-C_4)$alkoxycarbonyl-$(C_1-C_4)$alkyl, $(C_1-C_4)$alkylaminocarbonyl-$(C_1-C_4)$alkyl, $(C_1-C_4)$alkylcarbonyl, $(C_1-C_4)$alkoxycarbonyl, aminocarbonyl, $(C_1-C_4)$alkylaminocarbonyl, phenoxy-$(C_1-C_4)$alkyl, phenyl-$(C_1-C_4)$alkyl, heterocyclyl; heterocyclylamino, heterocyclyloxy, heterocyclylthio or one of the last-mentioned 16 radicals which is substituted in the acyclic moiety or, preferably, in the cyclic moiety by one or more radicals selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl, $(C_1-C_4)$alkoxy, heterocyclyl in the radicals containing in each case 3 to 9 ring atoms and 1 to 3 hetero ring atoms selected from the group consisting of N, O and S, or two adjacent radicals X together are a fused cycle which has 4 to 6 ring atoms and is carbocyclic or contains hetero ring atoms selected from the group consisting of O, S and N and which is unsubstituted or substituted by one or more radicals selected from the group consisting of halogen, $(C_1-C_4)$alkyl and oxo.

$(X)_n$ is especially preferably n substituents X, where X in each case independently of one another is halogen, OH, $NO_2$, CN, SCN $(C_1-C_6)$alkyl, $(C_1-C_6)$alkoxy, $(C_1-C_4)$alkylcarbonyl or $(C_1-C_4)$alkyloxycarbonyl, the last-mentioned four radicals being unsubstituted or substituted by halogen or $(C_1-C_4)$alkoxy, and very especially preferably n substituents X, where X in each case independently of one another is halogen, hydroxyl, $(C_1-C_4)$alkyl or $(C_1-C_4)$alkoxy.

Independently of one another, heterocyclyl in the radicals mentioned above or further below is preferably a heterocyclic radical having 3 to 7 ring atoms and 1 to 3 hetero atoms selected from the group consisting of N, O and S, preferably a heteroaromatic radical selected from the group consisting of pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl or a partially or fully hydrogenated heterocyclic radical selected from the group consisting of oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl. Heterocyclyl is especially preferably a heterocyclic radical having 3 to 6 ring atoms and one (1) heteroatom selected from the group consisting of N, O and S, in particular a heteroaromatic radical having 5 or 6 ring atoms or a saturated or partially unsaturated heterocyclic (not heteroaromatic) radical having 3 to 6 ring atoms.

Moreover, heterocyclyl is preferably a heterocyclic radical having 5 or 6 ring atoms and 2 or 3 heteroatoms selected from the group consisting of N, O and S, in particular pyrimidinyl, pyridazinyl, pyrazinyl, triazinyl, thiazolyl, thiadiazolyl, oxazolyl, isoxazolyl, pyrazolyl, imidazolyl, triazolyl or piperazinyl, dioxolanyl, oxazolinyl, isoxazolinyl, oxazolidinyl, isoxazolidinyl or morpholinyl.

Preferably, the number of the carbon atoms of the total of the carbon atoms of the two radicals $A^1$ and $A^2$—$R^2$ is a) at least 6 carbon atoms, in particular 6 to 20 carbon atoms, very especially 6 to 12 carbon atoms, or b) 5 carbon atoms, in which case $A^1$=a group of the formula —$CH_2$— or —$CH_2CH_2$— and $R^1$=($C_1$-$C_4$)alkyl, ($C_1$-$C_4$)haloalkyl, ($C_2$-$C_6$)haloalkenyl or ($C_3$-$C_9$)cycloalkyl which is unsubstituted or substituted, preferably, $R^1$=($C_1$-$C_4$)alkyl, ($C_1$-$C_4$)haloalkyl or ($C_3$-$C_6$)cycloalkyl which is unsubstituted or substituted by one or more radicals selected from the group consisting of ($C_1$-$C_4$)alkyl and ($C_1$-$C_4$)alkyl.

In particular, the total number of the carbon atoms of the radicals $A^1$ and $A^2$—$R^2$ together is one of the abovementioned alternative a).

The composite group —$A^2$—$R^2$ is preferably cyclopropyl (hereinbelow also "c-Pr"), $CH_2$-c-Pr, —$(CH_2)_2$-c-Pr, cyclobutyl (hereinbelow also "c-Bu"), $CH_2$-c-Bu; $(CH_2)_2$-c-Bu, oxiranyl, oxiranyl methyl or 2-(oxiranyl)-eth-1-yl.

The present invention also relates to processes for the preparation of the compounds of the formula (I) or their salts, which comprises a) reacting a compound of the formula (II)

 (II)

where Fu is a functional group selected from the group consisting of carboxylic ester, carboxylic orthoester, carboxylic acid chloride, carboxamide, carboxylic anhydride and trichloromethyl with a compound of the formula (III) or an acid addition salt thereof

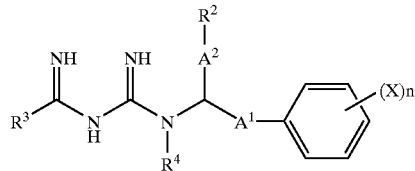 (III)

or b) reacting a compound of the formula (IV)

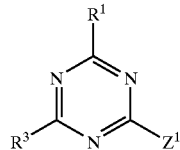 (IV)

where $Z^1$ is an exchangeable radical or leaving group, for example chlorine, trichloromethyl, ($C_1$-$C_4$)alkylsulfonyl and unsubstituted or substituted phenyl-($C_1$-$C_4$)alkylsulfonyl or ($C_1$-$C_4$)alkylphenylsulfonyl with a suitable amine of the formula (V) or an acid addition salt thereof

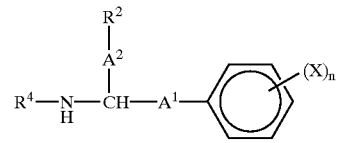 (V)

where, in formulae (II), (III), (IV) and (V), the radicals $R^1$, $R^2$, $R^3$, $R^4$, $A^1$, $A^2$ and X and n are as defined in formula (I).

The compounds of the formulae (II) and (III) are preferably reacted with base catalysis in an inert organic solvent such as, for example, tetrahydrofuran (THF), dioxane, acetonitrile, dimethylformamide (DMF), methanol and ethanol, at temperatures between −10° C. and the boiling point of the solvent, preferably at 20° C. to 60° C.; if acid addition salts of the formula (III) are used, they are, as a rule, liberated in situ with the aid of a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The base in question is employed, for example, in the range of 0.1 to 3 mol equivalents based on the compound of the formula (III). The compound of the formula (II) may be employed, for example, in equimolar amounts or in an excess of up to 2 mol equivalents relative to the compound of the formula (III). The principles of the processes in question are known from the literature (compare: Comprehensive Heterocyclic Chemistry, A. R. Katritzky, C. W. Rees, Pergamon Press, Oxford, N.Y., 1984, Vol.3; Part 2B; ISBN 0-08-030703-5, p.290).

The compounds of the formulae (IV) and (V) are preferably reacted with base catalysis in an inert organic solvent such as, for example, THF, dioxane, acetonitrile, DMF, methanol and ethanol, at temperatures between −10° C. and the boiling point of the solvent or solvent mixture in question, preferably at 20° C. to 60° C.; if the compound (V) is used as an acid addition salt, it is, if appropriate, liberated in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The base in question is employed, as a rule, in the range of 1 to 3 mol equivalents based on the compound of the formula (IV). The compound of the formula (IV) can be employed, for example, in equimolar amounts relative to the compound of the formula (V) or in an excess of up to 2 mol equivalents. The principles of the processes in question are known from the literature (cf. Comprehensive Heterocyclic Chemistry, A. R. Katritzky, C. W. Rees, Pergamon Press, Oxford, N.Y., 1984, Vol.3; Part 2B; ISBN 0-08-030703-5, p.482).

The starting materials of the formulae (II), (III), (IV) and (V) are either commercially available or can be prepared by, or analogously to, processes known from the literature. Some of the compounds of the formulae (III) and (V) are novel and also subject of the invention. Also, the compounds can be prepared, for example, by one of the processes described hereinbelow.

The compound of the formula (IV) or a direct precursor thereof can be prepared, for example, as follows:

1. The reaction of a compound of the formula (II) with an amidinothiourea derivative of the formula (VI)

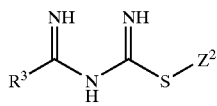 (VI)

where $Z^2$ is $(C_1-C_4)$alkyl or phenyl-$(C_1-C_4)$alkyl and $R^3$ is as defined in formula (I) affords compounds of the formula (IV) in which $Z^1=-SZ^2$.

2. The reaction of an amidine of the formula (VII) or of an acid addition salt thereof

where $R^1$ is as defined in formula (I)
with an N-cyanodithioiminocarbonate of the formula (VII)

in which $Z^3$ is $(C_1-C_4)$alkyl or phenyl-$(C_1-C_4)$alkyl affords compounds of the formula (IV) where $Z^1=-S-Z^3$.

3. The reaction of an alkali metal dicyanamide with a carboxylic acid derivative of the abovementioned formula (II) affords compounds of the formula (IV) where $Z^1=NH_2$.

4. The reaction of trichloroacetonitrile with a nitrile of the formula (IX)

where $R^1$ is as defined in formula (I) affords, initially, compounds of the formula (X)

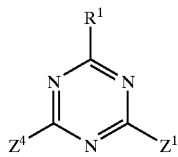 (X)

where $Z^1$ and $Z^4$ are each $CCl_3$, and these, when subsequently reacted with compounds of the formula H—$R^3$ ($R^3$ as in formula (I)), lead to compounds of the formula (IV) where $Z^1=CCl_3$.

The carboxylic acid derivatives of the formula (II) are reacted with the amidinothiourea derivatives of the formula (VI) in an organic solvent such as, for example, acetone, THF, dioxane, acetonitrile, DMF, methanol, ethanol, at temperatures of –10° C. to the boiling point of the solvent, preferably at 0° C. to 20° C., preferably with base catalysis. However, the reaction may also be carried out in water or aqueous solvent mixtures with one or more of the abovementioned organic solvents. If (VI) is employed as an acid addition salt, it may be liberated, if appropriate, in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The base in question is employed, for example, in the range of 1 to 3 mol equivalents based on the compound of the formula (VI). Compounds of the formulae (II) and (VI) can be employed, for example, in equimolar amounts or in an excess of up to 2 mol equivalents of the compound of the formula (II). The principles of the processes in question are known from the literature (cf. H. Eilingsfeld, H. Scheuermann, Chem. Ber.; 1967, 100, 1874), the corresponding intermediates of the formula (IV) are novel.

The amidines of the formula (VII) are reacted with the N-cyanodithioiminocarbonates of the formula (VII) in an inert organic solvent such as, for example, acetonitrile, DMF, dimethylacetamide(DMA), N-methylpyrrolidone (NMP), methanol and ethanol, at temperatures from –10° C. to the boiling point of the solvent, preferably at 20° C. to 80° C., preferably with base catalysis. If (VII) is employed as an acid addition salt, it may be liberated, if appropriate, in situ using a base. Suitable bases or basic catalysts are alkali metal hydroxides, alkali metal hydrides, alkali metal carbonates, alkali metal alkoxides, alkaline earth metal hydroxides, alkaline earth metal hydrides, alkaline earth metal carbonates or organic bases such as triethylamine or 1,8-diazabicyclo[5.4.0]undec-7-ene (DBU). The base in question is employed, for example, in the range of 1 to 3 mol equivalents based on the compound of the formula (VIII), compounds of the formulae (VII) and (VIII) can be employed, as a rule, in equimolar amounts or with an excess of 2 mol equivalents of the compound of the formula (VII). The principles of the processes in question are known from the literature (cf. T. A. Riley, W. J. Henney, N. K. Dalley, B. E. Wilson, R. K. Robins; J. Heterocyclic Chem.; 1986, 23 (6), 1706–1714), the corresponding intermediates of the formula (IV) are novel.

Intermediates of the formula (X) where $Z^1$=chlorine can be prepared by reacting alkali metal dicyanamide with a carboxylic acid derivative of the formula (II), in which case Fu is preferably the functional group carboxylic acid chloride or carboxamide. The reactants are reacted for example with acid catalysis in an inert organic solvent such as, for example, toluene, chlorobenzene, chlorinated hydrocarbons at temperatures between –10° C. and the boiling point of the solvent, preferably at 20° C. to 80° C., it being possible for the intermediates which form to be chlorinated in situ using a suitable chlorinating reagent such as, for example, phosphorus oxychloride. Suitable acids are, for example, hydrohalic acids such as HCl or else Lewis acids such as, for example $AlCl_3$ or $BF_3$ (cf. U.S. Pat. No. 5,095,113, Du Pont).

Intermediates of the formula (X) where $Z^1$, $Z^4$=trihalomethyl can be prepared by reacting the corresponding trihaloacetonitriles with a carbonitrile of the formula (IX). The reactants are reacted, for example, with acid catalysis in an inert organic solvent such as, for example, toluene, chlorobenzene, chlorinated hydrocarbons at temperatures between –40° C. and the boiling point of the solvent, preferably at –10° C. to 30° C. Examples of suitable acids are hydrohalic acids such as HCl or else Lewis acids such as, for example, $AlCl_3$ or $BF_3$ (cf. EP-A-130939, Ciba Geigy).

Intermediates of the formula (IV) where $Z^1=(C_1-C_4)$ alkylmercapto or unsubstituted phenyl-$(C_1-C_4)$ alkylmercapto can be converted with a suitable chlorinating reagent such as, for example, elemental chlorine or phosphorus oxychloride in an inert organic solvent such as, for example, toluene, chlorobenzene, chlorinated hydrocarbons or others at temperatures between –40° C. and the boiling point of the solvent, preferably at 20° C. to 80° C., to give more reactive chlorotriazines of the formula (IV) where $Z^1$=Cl (cf. J. K. Chakrabarti, D. E. Tupper; Tetrahedron 1975, 31(16), 1879–1882).

Intermediates of the formula (IV) where $Z^1$=($C_1$–$C_4$) alkylmercapto or unsubstituted or substituted phenyl-($C_1$–$C_4$)alkylmercapto or ($C_1$–$C_4$)alkylphenylthio can be oxidized with a suitable oxidizing reagent such as, for example, m-chloroperbenzoic acid, hydrogen peroxide, potassium peroxomonosulfate in a suitable solvent such as, for example, chlorinated hydrocarbons, acetic acid, water, alcohols, acetone or mixtures of these at temperatures between 0° C. and the boiling point of the solvent, preferably 20° C. to 80° C. (cf. T. A. Riley, W. J. Henney, N. K Dalley, B. E. Wilson, R. K. Robins; J. Heterocyclic Chem.; 1986, 23 (6), 1706–1714).

Acids which are suitable for preparing the acid addition salts of the compounds of the formula (I) are the following: hydrohalic acids such as hydrochloric acid or hydrobromic acid, furthermore phosphoric acid, nitric acid, sulfuric acid, mono- or bifunctional carboxylic acids and hydroxycarboxylic acids such as acetic acid, maleic acid, succinic acid, fumaric acid, tartaric acid, citric acid, salicylic acid, sorbic acid or lactic acid, and also sulfonic acids such as p-toluenesulfonic acid or 1,5-naphthalenedisulfonic acid. The acid addition compounds of the formula (I) can be obtained in a simple manner by the customary salt formation methods, for example by dissolving a compound of the formula (I) in a suitable organic solvent such as, for example, methanol, acetone, methylene chloride or benzine, and adding the acid at temperatures from 0 to 100° C., and they can be isolated in the known manner, for example by filtration, and, if appropriate, purified by washing with an inert organic solvent.

The base addition salts of the compounds of the formula (I) are preferably prepared in inert polar solvents such as, for example, water, methanol or acetone at temperatures from 0 to 100° C. Examples of bases which are suitable for the preparation of the salts according to the invention are alkali metal carbonates such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide, potassium tert-butoxide, or ammonia or ethanolamine. Quarternary ammonium salts can be prepared, for example, by double decomposition or condensation with quarternary ammonium salts of the formula [NRR'R"R'"]$^+$ X$^-$ where R, R', R" and R'" independently of one another are ($C_1$–$C_4$)alkyl, phenyl or benzyl and X$^-$ is an anion, for example Cl$^-$ or OH$^-$.

Solvents termed "inert solvents" in the above process variants are to be understood as meaning in each case solvents which are inert under the reaction conditions in question, but which need not be inert under any reaction conditions.

The compounds of the formula (I) according to the invention and their salts, all termed hereinbelow as compounds of the formula (I) (according to the invention), have an excellent herbicidal activity against a broad range of economically important monocotyledonous and dicotyledonous harmful plants. The active substances also act efficiently on perennial weeds which produce shoots from rhizomes, root stocks or other perennial organs and which are difficult to control. In this context, it does not matter whether the substances are applied pre-planting, pre-emergence or post-emergence.

Specifically, examples may be mentioned of some representatives of the monocotyledonous and dicotyledonous weed flora which can be controlled by the compounds according to the invention, without the enumeration being a restriction to certain species.

Examples of weed species on which the active substance acts efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum,* and also perennial *Cyperus* species.

In the case of the dicotyledonous weed species, the range of action extends to species such as, for example, *Galium, Viola, Veronica, Lamium, Stellaria, Amaranthus, Sinapis, Ipomoea, Matricaria, Abutilon* and *Sida* from amongst the annuals, and *Convolvulus, Cirsium, Rumex* and *Artemisia* in the case of the perennial weeds.

The active substances according to the invention likewise effect outstanding control of weeds which occur under the specific conditions of rice growing, such as, for example, *Sagittaria, Alisma, Eleocharis, Scirpus* and *Cyperus.*

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledonous and dicotyledonous weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use, inclusive of ornamental plantings.

In addition, the substances according to the invention have excellent growth-regulating properties in crop plants. They engage in the plant metabolism in a regulating manner and can thus be employed for the targeted control of plant constituents and for facilitating harvesting, such as, for example, by provoking desiccation and stunted growth. Furthermore, they are also suitable for generally regulating and inhibiting undesired vegetative growth, without simultaneously destroying the plants. Inhibition of vegetative growth plays an important role in many monocotyledonous and dicotyledonous crops because lodging can be reduced hereby, or prevented completely.

Due to their herbicidal and plant-growth regulatory properties, the active substances can also be employed for controlling harmful plants in crops of known genetically modified plants, or genetically modified plants yet to be developed. As a rule, the transgenic plants are distinguished by particular advantageous properties, for example by resistances to certain pesticides, mainly certain herbicides, resistances to plant diseases or pathogens of plant diseases, such as certain insects or microorganisms such as fungi, bacteria or viruses. Other particular properties relate, for example, to the harvested material with regard to quantity, quality, storage properties, composition and specific constituents.

Thus, transgenic plants are known where the starch content is increased or the starch quality is altered or those where the harvested material has a different fatty acid spectrum.

The compounds of the formula (I) according to the invention or their salts are preferably employed in economically important transgenic crops of useful plants and ornamentals, for example cereals such as wheat, barley, rye, oats, sorghum and millet, rice, cassava and maize, or else crops of sugar beet, cotton, soya, oil seed rape, potatoes, tomatoes, peas and other vegetables.

The compounds of the formula (I) can preferably be employed as herbicides in crops of useful plants which are resistant to the phytotoxic effects of the herbicides or have been rendered thus by means of genetic engineering.

Traditional ways of generating novel plants which have modified characteristics in comparison with existing plants consist, for example, in traditional breeding methods and the generation of mutants. However, it is also possible to generate novel plants with altered characteristics with the aid of genetic engineering methods (see, for example, EP-A-0221044, EP-A-0131624). For example, several cases have been described of genetic engineering modifications of crop plants with the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659), transgenic crop plants, for example cotton, which are capable of producing *Bacillus thuringiensis* toxins (Bt toxins) which make the plants resistant to specific pests (EP-A-0142924, EP-A-0193259), transgenic crop plants whose fatty acid spectrum is modified (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423–431).

In order to perform such genetic engineering manipulations, nucleic acid molecules may be introduced into plasmids which allow mutagenesis or a sequence change by means of recombination of DNA sequences. It is possible, for example, with the aid of the abovementioned standard methods to perform base exchanges, to remove subsequences or to add natural or synthetic sequences. To connect the DNA fragments to each other, adaptors or linkers may be attached to the fragments. For example, plant cells with a reduced activity of a gene product can be generated by expressing at least one corresponding antisense RNA, a sense RNA to achieve a cosuppressory effect or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, on the other hand DNA molecules which only encompass parts of the coding sequence, but these parts must be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells may be regenerated by known techniques to give complete plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The compounds (I) according to the invention can preferably be employed in transgenic crops which are resistant to herbicides from the group of the sulfonylureas, glufosinate-ammonium or glyphosate-isopropylammonium and analogous active substances.

When the active substances according to the invention are used in transgenic crops, effects other than the herbicidal effects to be observed in other crops are frequently found which are specific for application in the particular transgenic crop, for example an altered or specifically widened weed spectrum which can be controlled, altered application rates which may be employed for application, preferably good combining ability with the herbicides to which the transgenic crop is resistant, and an effect on growth and yield of the transgenic crop plants.

The invention therefore also relates to the use of the compounds (I) according to the invention as herbicides for controlling harmful plants in transgenic crop plants.

The use according to the invention for controlling harmful plants or for regulating the growth of plants also includes the case where the active substance of the formula (I) or a salt thereof is only formed in the plant or the soil from a precursor ("prodrug") after its application to the plant.

The compounds according to the invention can be employed in the conventional preparations as wettable powders, emulsifiable concentrates, sprayable solutions, dusts or granules. The invention therefore also relates to herbicidal and plant-growth-regulating compositions which comprise compounds of the formula (I).

The compounds of the formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küichler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Wettable powders are preparations which are uniformly dispersible in water and which, besides the active substance, also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the herbicidal active substances are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the active substance in an organic solvent, for example butanol, cyclohexanone, dimethyl-formamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). The active substance concentration in wettable powders is, for example, approximately 10 to 90% by weight, the remainder to 100% by weight being composed of customary formulation components. In the case of emulsifiable concentrates, the active substance concentration can amount to approximately 1 to 90, preferably 5 to 80, % by weight. Formulations in the form of dusts usually comprise 1 to 30% by weight of active substance, preferably in most cases 5 to 20% by weight of active substance, while sprayable solutions comprise approximately 0.05 to 80, preferably 2 to 50, % by weight of active substance. In the case of water-dispersible granules, the active substance content depends partly on whether the active compound is in liquid or solid form and on which granulation auxiliaries, fillers and the like are being used. The water-dispersible granules, for example, comprise between 1 and 95% by weight of active substance, preferably between 10 and 80% by weight.

In addition, the active substance formulations mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Active substances which can be employed as components in mixed formulations or in a tank mix, together with the active substances according to the invention, are, for example, known active substances as they are described in, for example, Weed Research 26, 441–445 (1986), or "The Pesticide Manual", 10th edition, The British Crop Protection Council and the Royal Soc. of Chemistry, 1994 and the literature cited therein. Herbicides which are known from the literature and which may be combined with the compounds of the formula (I) are, for example, the following active substances (note: the compounds are either designated by the "common name" of the International Organization for Standardization (ISO) or by the chemical name, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethylthiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl] ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S482); flumipropyn; flupoxam (KNW-739); fluorodifen; fluoroglycofen-ethyl; flupropacil (UBIC4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazol; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazol-1-carboxamide; thenylchlor (NSK-850); thiazafluron; thizopyr (Mon-13200); thidiazimin (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX46037); trimeturon; tsitodef; vernolate; WL 110547, i.e. 5-phenoxy-1-[3-(trifluoromethyl)phenyl]-1H-tetrazole; UBH-509; D489; LS 82-556; KPP-300; NC-324; NC-330; KH-218; DPX-N8189; SC-0774; DOWCO-535; DK-8910; V-53482; PP600; MBH-001; KIH-9201; ET-751; KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Preparations in the form of dusts, soil granules, granules for broadcasting and sprayable solutions are conventionally not diluted further with other inert substances prior to use.

The application rate required of the compounds of the formula (I) varies with the external conditions such as, inter alia, temperature, humidity and the nature of the herbicide used. It may vary within wide limits, for example between 0.001 and 10.0 kg/ha or more of active substance, but it is preferably between 0.005 and 5 kg/ha.

Quantities (also percentages) in the following examples are weight-based, unless otherwise specified.

A. CHEMICAL EXAMPLES

Example A1

2-Amino-4-(1-fluoro-1-methylethyl)-6-(3-phenyl-1-cyclobutyl-1-propylamino)-1,3,5-triazine (see Table 4, Example 4-2)

A solution prepared from 0.32 g (0.014 mol) of sodium and 10 ml of methanol is added to 1.90 g (0.00613 mol) of 3-phenyl-1-cyclobutyl-1-(biguanidino)propane hydrochloride in 30 ml of methanol and 2 g of molecular sieve 3 Å (Ångström). Then, 1.10 g (0.0092 mol) of methyl 1-fluoro-1-methylpropionate are added dropwise and the mixture is stirred first for 2 hours at 25° C. and then for 4 hours at 65° C. The reaction mixture is filtered, the filtrate is concentrated and the residue is taken up in ethyl acetate. The mixture is washed with water and dried with sodium sulfate. The dessicant is filtered off with suction and the solvent is evaporated in vacuo. After purification by column chromatography (eluant: ethyl acetate), 1.66 g (79% of theory) of 2-amino-4-(1-fluoro-1-methylethyl)-6-(3-phenyl-1-cyclobutyl-1-propylamino)-1,3,5-triazine are obtained.

Example A2

2-Amino-4-(1-fluoro-1-methylethyl)-6-(1-phenyl-4-cyclopropyl-4-butylamino)-1,3,5-triazine (see Example 22-12, Table 22)

1.52 g (0.008 mol) of 2-amino-4-chloro-6-(1-fluoro-1-methylethyl)-1,3,5-triazine and 1.64 g (0.012 mol) of potassium carbonate are introduced into 30 ml of acetonitrile. 1.50 g (0.008 mol) of 4-phenyl-1-cyclopropyl-1-butylamine, dissolved in 10 ml of acetonitrile, are added dropwise to this solution. The mixture is refluxed for three hours. The solid components are then filtered off with suction and the filtrate is evaporated on a rotary evaporator. The residue is purified by column chromatography (eluant: methyl acetate). This gives 2.36 g (86% of theory) of 2-amino-4-(1-fluoro-1-methylethyl)-6-(1-phenyl-4-cyclopropyl-4-butylamino)-1,3,5-triazine.

Example A3

2-Amino-4-(1-fluoro-1-methylethyl)-6-[3-(3,5-dimethylphenyl)-1-cyclopropyl-1-propylamino]-1,3,5-triazine (see Table 9, Ex. 9–17)

A methoxide solution prepared from 1.2 g (0.05 mol) of sodium and 100 ml of methanol is added to 8.1 g (0.025 mol) of 3-(3,5-dimethylphenyl)-1-cyclopropyl-1-(1-biguanidino)propane hydrochloride in 50 ml of methanol and 7 g of ground molecular sieve 3 Å. Then, 5.4 g (0.045 mol) of methyl 1-fluoro-1-methylpropionate are added and the mixture is stirred for 2 hours at 25° C. and then for 4 hours at 65° C. The reaction mixture is filtered, the filtrate is concentrated and the residue is taken up in ethyl acetate. The mixture is washed with water and dried with sodium sulfate. The dessicant is filtered off and the solvent is evaporated in vacuo. After purification by column chromatography (eluant: ethyl acetate), 7.4 g (83% of theory) of 2-amino-4-(1-fluoro-1-fluoro-1-methylethyl)-6-[3-(3,5-dimethyl)-1-cyclopropyl-1-propylamino)-1,3,5-triazine are obtained.

Example A4

2-Amino-6-methyl-4-[3-(3-methylphenyl)-1-cyclobutyl-1-propylamino]1,3,5-triazine (see Table 4, Ex. 4–29)

2.2 g (0.015 mol) of 2-amino-4-chloro-methyl-1,3,5-triazine and 4.1 g (0.03 mol) of K$_2$CO$_3$ are introduced into 50 ml of acetonitrile. 2.5 g (0.015 mol) of 3-(3-methylphenyl)-1-cyclobutyl-1-propylamine, dissolved in 20 ml of acetonitrile, are added dropwise to this solution. The mixture is then refluxed for 3 hours. The solid constituents are subsequently filtered off with suction and the filtrate is evaporated on a rotary evaporator. The residue is purified by means of column chromatography (eluant: ethyl acetate). This gives 4.3 g (92% of theory) of 2-amino-6-methyl-4-[3-(3-methylphenyl)-1-cyclobutyl-1-propylamino]-1,3,5-triazine.

Example A5

2-Amino-4-(1-fluoro-1-methylethyl)-6-[4-(3,5-dimethylphenyl)-1-cyclopropyl-1-butylamino]-1,3,5-triazine (see Table 22, Ex. 22–28)

A methoxide solution prepared from 1.2 g (0.05 mol) of sodium and 100 ml of methanol is added to 8.4 g (0.025 mol) of 4-(3,5-dimethylphenyl)-1-cyclopropyl-1-(1-biguanidino)butane hydrochloride in 50 ml of methanol and 7 g of ground molecular sieve 3 Å. 5.4 g (0.045 mol) of methyl 1-fluoro-1-methyl-propionate are then added and the mixture is stirred for 2 hours at 25° C. and then for 4 hours at 65° C. The reaction mixture is filtered, the filtrate is concentrated and the residue is taken up in ethyl acetate. The mixture is washed with water and dried with sodium sulfate. The dessicant is filtered off and the solvent is evaporated in vacuo. After purification by column chromatography (eluant: ethyl acetate), 7.7 g (83% of theory) of 2-amino-4-(1-fluoro-1-fluoro-1-methylethyl)-6-[3-(3,5-dimethyl)-1-cyclopropyl-1-butylamino]-1,3,5-triazine are obtained.

The compounds described in Tables 1 to 44 below are obtained by or analogously to the above Examples A1 to A5 or by the methods described further above in general terms. The abbreviations in the tables denote:

Me=methyl

Et=ethyl

Pr=propyl i-Pr=isopropyl c-Pr=cyclopropyl c-Bu=cyclobutyl t-Bu=tertiary-butyl c-Hexyl=cyclohexyl

A1=(CH$_2$)$_1$=—CH$_2$—

A2=(CH$_2$)$_2$=—CH$_2$CH$_2$—

A3=(CH$_2$)$_3$=—CH$_2$CH$_2$CH$_2$—

| A4 | = | (CH$_2$)$_4$ | = | —CH$_2$CH$_2$CH$_2$CH$_2$— |
|---|---|---|---|---|
| Ac | = | COCH$_3$ | = | acetyl |
| Ox | = | | = | oxiranyl |

Ph=phenyl
(X)$_n$="—" means n=0

The Tables 1 to 41 which follow relate to formula (I)

TABLE 1

(1)

| No. | R$^1$ | —A$^2$—R$^2$ | A$^1$ | (X)$_n$ | Physical data |
|---|---|---|---|---|---|
| 1-1 | CH$_2$-i-Pr | CH$_2$-c-Pr | A1 | — | oil |
| 1-2 | CFMe$_2$ | CH$_2$-c-Pr | A1 | — | oil |
| 1-3 | i-Pr | CH$_2$-c-Pr | A1 | — | oil |
| 1-4 | i-Pr | CH$_2$-c-Bu | A1 | — | |
| 1-5 | CFMe$_2$ | CH$_2$-c-Bu | A1 | — | |
| 1-6 | Me | CH$_2$-c-Bu | A1 | — | |
| 1-7 | CFMe$_2$ | CH$_2$-c-Bu | A1 | 3-Me | |
| 1-8 | CFMe$_2$ | CH$_2$CH$_2$-c-Pr | A1 | — | |
| 1-9 | i-Pr | CH$_2$CH$_2$-c-Pr | A1 | | |
| 1-10 | CFMe$_2$ | CH$_2$CH$_2$-c-Bu | A1 | | |
| 1-11 | i-Pr | CH$_2$CH$_2$-c-Bu | A1 | | |

TABLE 2

| No. | R$^1$ | —A$^2$—R$^2$ | A$^1$ | (X)$_n$ | Physical data |
|---|---|---|---|---|---|
| 2-1 | c-Pr | 2,2-Cl$_2$-c-Pr | A2 | 3-Cl, 5-F | |
| 2-2 | CFMe$_2$ | " | " | 3-Me | |
| 2-3 | CClMe$_2$ | " | " | 3-Me | |
| 2-4 | CFMe$_2$ | " | " | 3-Cl | |
| 2-5 | i-Pr | " | " | 3-Cl | |
| 2-6 | CFMe$_2$ | " | " | 3-F | |
| 2-7 | CHF$_2$ | " | " | 3-F | |
| 2-8 | CFMe$_2$ | " | " | 3-OMe | |
| 2-9 | CClMe$_2$ | " | " | 3-OMe | |
| 2-10 | CFMe$_2$ | " | CH$_2$CHMe | — | |
| 2-11 | CClMe$_2$ | " | CH$_2$CHMe | — | |

TABLE 3

| No. | R$^1$ | —A$^2$—R$^2$ | A$^1$ | (X)$_n$ | Physical data |
|---|---|---|---|---|---|
| 3-1 | CFMe$_2$ | 2-OMe-c-Pr | A2 | — | |
| 3-2 | CFMe$_2$ | 2-OEt-c-Pr | A2 | — | |
| 3-3 | CF$_3$ | 2,2-(OMe)$_2$-c-Pr | A2 | — | |
| 3-4 | CH$_2$F | 2,2-(OEt)$_2$-c-Pr | A2 | — | |

TABLE 4

| No. | R$^1$ | —A$^2$—R$^2$ | A$^1$ | (X)$_n$ | Physical data |
|---|---|---|---|---|---|
| 4-1 | i-Pr | c-Bu | A2 | — | oil |
| 4-2 | CFMe$_2$ | c-Bu | A2 | — | oil |
| 4-3 | Me | c-Bu | A2 | — | oil |
| 4-4 | Et | c-Bu | A2 | — | |
| 4-5 | Pr | c-Bu | A2 | — | |
| 4-6 | Bu | c-Bu | A2 | — | |
| 4-7 | Ph | c-Bu | A2 | — | |
| 4-8 | CH$_2$—C$_6$H$_5$ | c-Bu | A2 | — | |
| 4-9 | c-Pr | c-Bu | A2 | — | |
| 4-10 | i-Pr | c-Bu | A2 | 3-Cl | oil |
| 4-11 | CFMe$_2$ | c-Bu | A2 | 3-Cl | oil |
| 4-12 | CF$_3$ | c-Bu | A2 | 3-Cl | |
| 4-13 | CF$_3$ | c-Bu | A2 | — | |
| 4-14 | i-Pr | c-Bu | A2 | 3-Me | oil |
| 4-15 | CFMe$_2$ | c-Bu | A2 | 3-Me | oil |
| 4-16 | CF$_3$ | c-Bu | A2 | 3-Me | |
| 4-17 | CCl$_3$ | c-Bu | A2 | 3-Me | |
| 4-18 | Me | c-Bu | A2 | 2-Me | |
| 4-19 | Et | c-Bu | A2 | 2-Me | |
| 4-20 | CH$_2$-i-Pr | c-Bu | A2 | 2-Me | |
| 4-21 | C$_6$H$_5$ | c-Bu | A2 | 2,4-Cl$_2$ | |
| 4-22 | CH$_2$—Ph | c-Bu | A2 | 4-NO$_2$ | |
| 4-23 | i-Pr | c-Bu | A2 | 3-OMe | oil |
| 4-24 | CFMe$_2$ | c-Bu | A2 | 3-OMe | oil |
| 4-25 | CFMe$_2$ | c-Bu | A2 | 2-Me | oil |
| 4-26 | i-Pr | c-Bu | A2 | 2-Me | oil |
| 4-27 | i-Pr | c-Bu | A2 | 3-F | oil |
| 4-28 | CFMe$_2$ | c-Bu | A2 | 3-F | oil |
| 4-29 | Me | c-Bu | A2 | 3-Me | oil |

TABLE 5

| No. | R$^1$ | —A$^2$—R$^2$ | A$^1$ | (X)$_n$ | Physical data |
|---|---|---|---|---|---|
| 5-1 | CFMe$_2$ | 2,2,3,3-F$_4$-c-Bu | A2 | — | |
| 5-2 | CHFMe | " | A2 | — | |
| 5-3 | CF(CF$_3$)$_2$ | " | A2 | — | |
| 5-4 | CClMe$_2$ | " | A2 | — | |
| 5-5 | i-Pr | " | A2 | — | |

TABLE 6

| No. | R$^1$ | —A$^2$—R$^2$ | A$^1$ | (X)$_n$ | Physical data |
|---|---|---|---|---|---|
| 6-1 | CFMe$_2$ | 3-OH-c-Bu | A2 | — | |
| 6-2 | i-Pr | " | A2 | — | |
| 6-3 | CFMe$_2$ | " | A2 | 3-Me | |
| 6-4 | CF$_3$ | " | A2 | 3-Me | |
| 6-5 | Et | " | A2 | 3,5-Me$_2$ | |
| 6-6 | Et | " | A2 | 3,5-Me$_2$ | |
| 6-7 | CFMe$_2$ | 3-Ac-c-Bu | A2 | — | |
| 6-8 | CFMe$_2$ | 3-OCH$_3$—C$_6$H$_4$-c-Bu | A2 | — | |
| 6-9 | Me | 3,3-F$_2$-c-Bu | A2 | — | |
| 6-10 | Pr | " | A2 | — | |
| 6-11 | CFMe$_2$ | " | A2 | — | |
| 6-12 | Et | " | A2 | — | |
| 6-13 | CF$_3$ | " | A2 | — | |
| 6-14 | CH$_2$F | 3-Me-c-Bu | A2 | — | |
| 6-15 | CF$_3$ | 3-Me-c-Bu | A2 | — | |

TABLE 7

| No. | R$^1$ | —A$^2$—R$^2$ | A$^1$ | (X)$_n$ | Physical data |
|---|---|---|---|---|---|
| 7-1 | CFMe$_2$ | ◇=CH$_2$ | A2 | — | |
| 7-2 | i-Pr | ◇=CH$_2$ | A2 | — | |
| 7-3 | CF$_3$ | ◇=CH$_2$ | A2 | — | |

TABLE 7-continued

| No. | R¹ | —A²—R² | A¹ | (X)ₙ | Physical data |
|---|---|---|---|---|---|
| 7-4 | CH₂F | [diamond]=CH₂ | A2 | — | |
| 7-5 | CClMe₂ | [diamond]=CH₂ | A2 | — | |

TABLE 8

| No. | R¹ | —A²-R² | A¹ | (X)ₙ | Physical data |
|---|---|---|---|---|---|
| 8-1 | i-Pr | c-Pentyl | A2 | — | oil |
| 8-2 | CFMe₂ | c-Pentyl | A2 | — | oil |

TABLE 9

| No. | R¹ | —A²—R² | A¹ | (X)ₙ | Physical data |
|---|---|---|---|---|---|
| 9-1 | CH₂-i-Pr | c-Pr | A2 | — | oil |
| 9-2 | Et | c-Pr | A2 | — | oil |
| 9-3 | Me | c-Pr | A2 | — | oil |
| 9-4 | CMe₂C≡N | c-Pr | A2 | — | oil |
| 9-5 | CFMe₂ | c-Pr | A2 | 3-F | oil |
| 9-6 | CFMe₂ | c-Pr | A2 | 3-CF₃ | oil |
| 9-7 | i-Pr | c-Pr | A2 | 3-Cl | oil |

TABLE 9-continued

| No. | R¹ | —A²—R² | A¹ | (X)ₙ | Physical data |
|---|---|---|---|---|---|
| 9-8 | CFMe₂ | c-Pr | A2 | 3-Cl | oil |
| 9-9 | i-Pr | c-Pr | A2 | — | " |
| 9-10 | CFMe₂ | c-Pr | A2 | — | " |
| 9-11 | i-Pr | c-Pr | A2 | 3-CF₃ | " |
| 9-12 | i-Pr | c-Pr | A2 | 3-Me | " |
| 9-13 | i-Pr | c-Pr | A2 | 3-OMe | " |
| 9-14 | CFMe₂ | c-Pr | A2 | 3-OMe | " |
| 9-15 | CH₂-i-Pr | c-Pr | A2 | 3-Me | " |
| 9-16 | CFMe₂ | c-Pr | A2 | 3-Me | " |
| 9-17 | CFMe₂ | c-Pr | A2 | 3,5-Me₂ | " |
| 9-18 | i-Pr | c-Pr | A2 | 3,5-Me₂ | " |
| 9-19 | C₆H₅ | c-Pr | A2 | — | " |
| 9-20 | CFMe₂ | c-Pr | —CH₂—CO— | — | " |
| 9-21 | i-Pr | c-Pr | —CH₂—CO— | — | " |
| 9-22 | CF(CF₃)₂ | c-Pr | —CH₂—CO— | — | " |

TABLE 10

| No. | R¹ | —A²—R² | A¹ | (X)ₙ | Physical data |
|---|---|---|---|---|---|
| 10-1 | CFMe₂ | 2,2-Me₂-c-Pr | A2 | — | oil |
| 10-2 | i-Pr | " | A2 | — | |
| 10-3 | CFMe₂ | " | A2 | 3-Cl | |
| 10-4 | C(F)(OMe)-CF₃ | " | A2 | 3-Cl | |
| 10-5 | CH₃ | " | A2 | 2,3-Cl₂ | |
| 10-6 | CFMe₂ | " | A2 | 3,5-F₂ | |
| 10-7 | CFMe₂ | " | A2 | 3-F | |
| 10-8 | i-Pr | " | A2 | 3-F | |
| 10-9 | CFMe₂ | " | A2 | 3-OMe | |
| 10-10 | CF₃ | " | A2 | 3-OMe | |
| 10-11 | CFMe₂ | " | A2 | 3-Me | |
| 10-12 | CH₂CHF₂ | " | A2 | 3-Me | |
| 10-13 | CFMe₂ | " | [dioxolane ring structure] | — | |
| 10-14 | CF₃ | " | [dioxolane ring structure] | — | |
| 10-15 | CHF₂ | " | CH₂—CHMe— | — | |
| 10-16 | CClMe₂ | " | CH₂—CHMe— | — | |

TABLE 11

| No. | R¹ | —A²—R² | A¹ | (X)ₙ | Physical data |
|---|---|---|---|---|---|
| 11-1 | CFMe₂ | 2,2-F₂-c-Pr | A2 | — | |
| 11-2 | CH₃ | " | A2 | — | |
| 11-3 | CFMe₂ | " | A2 | 3-Cl | |
| 11-4 | i-Pr | " | A2 | 3-Cl | |
| 11-5 | CFMe₂ | " | A2 | 3-F | |
| 11-6 | CF(CF₃)₂ | " | A2 | 3-F | |
| 11-7 | CFMe₂ | " | A2 | 3-OMe | |

TABLE 11-continued

| No. | R¹ | —A²—R² | A¹ | (X)ₙ | Physical data |
|---|---|---|---|---|---|
| 11-8 | CH₂-i-Pr | " | A2 | 3-OMe | |
| 11-9 | CFMe₂ | " | A2 | 3-CF₃ | |
| 11-10 | CFMe₂ | " | A2 | 3-CCl₃ | |
| 11-11 | CFMe₂ | " | —CH₂CHOH— | — | |
| 11-12 | C(OMe)Me₂ | " | —CH₂CHOH— | — | |
| 11-13 | CClMe₂ | " | —CH₂CHOAc— | — | |
| 11-14 | Me | " | —CH₂CHOAc— | — | |

TABLE 12

| No. | R¹ | —A²—R² | A¹ | (X)ₙ | Physical data |
|---|---|---|---|---|---|
| 12-1 | CFMe₂ | 2,2-Br₂-c-Pr | A2 | — | |
| 12-2 | CF₂CHF₂ | 2,2-Br₂-c-Pr | A2 | — | |

TABLE 13

| No. | R¹ | —A²—R² | A¹ | (X)ₙ | Physical data |
|---|---|---|---|---|---|
| 13-1 | Me | c-Hexyl | A2 | — | |
| 13-2 | CH₂F | " | A2 | — | |
| 13-3 | CF₃ | " | A2 | 3-OH | |
| 13-4 | CCl₃ | " | A2 | 3-OEt | |
| 13-5 | CHFMe | " | A2 | 3-OPh | |
| 13-6 | c-Pr | " | A2 | — | |
| 13-7 | CH₂—C₆H₅ | " | A2 | — | |

TABLE 14

| No. | R¹ | —A²—R² | A¹ | (X)ₙ | Physical data |
|---|---|---|---|---|---|
| 14-1 | Me | Ox | A2 | — | |
| 14-2 | Et | Ox | A2 | — | |
| 14-3 | Pr | Ox | A2 | — | |
| 14-4 | i-Pr | Ox | A2 | — | |
| 14-5 | CFMe₂ | Ox | A2 | — | |
| 14-6 | CF₃ | Ox | A2 | 3-Cl | |
| 14-7 | CFMe₂ | Ox | A2 | 3-Cl | |
| 14-8 | i-Pr | Ox | A2 | 3-Cl | |
| 14-9 | CFMe₂ | Ox | A2 | 3-OMe | |
| 14-10 | i-Pr | Ox | A2 | 3-OMe | |
| 14-11 | CFMe₂ | Ox | A2 | 3-F | |
| 14-12 | i-Pr | Ox | A2 | 3-F | |

TABLE 15

| No. | R¹ | —A²—R² | A¹ | (X)ₙ | Physical data |
|---|---|---|---|---|---|
| 15-1 | CFMe | 1-Me—Ox | A2 | — | |
| 15-2 | i-Pr | 1-Me—Ox | A2 | — | |
| 15-3 | Me | 1-Me—Ox | A2 | — | |
| 15-4 | c-Pr | 1-Me—Ox | A2 | — | |
| 15-5 | Ox | 1-Me—Ox | A2 | 2-NO₂ | |

TABLE 16

| No. | R¹ | —A²—R² | A¹ | (X)ₙ | Physical data |
|---|---|---|---|---|---|
| 16-1 | n-Pr | 1,2-Me₂—Ox | A2 | 3-OH | |
| 16-2 | 3,5-Cl₂—C₆H₃ | 1,2-Me₂—Ox | A2 | 4-OH | |
| 16-3 | c-Pr | 2-Me—Ox | A2 | 5-OEt | |
| 16-4 | CH₂-4-Cl—C₆H₄ | 2-Me—Ox | A2 | 5-SMe | |

TABLE 17

| No. | R¹ | —A²—R² | A¹ | (X)ₙ | Physical data |
|---|---|---|---|---|---|
| 17-1 | CFMe₂ | 2-methyloxazolyl | A2 | — | |
| 17-2 | CF₂CHF₂ | 2-methylthiazolyl | A2 | — | |
| 17-3 | CH₂Ph | N-pyrrolyl | A2 | — | |

TABLE 18

| No. | R¹ | —A²—R² | A¹ | (X)ₙ | Physical data |
|---|---|---|---|---|---|
| 18-1 | CFMe₂ | 3-Furyl | A2 | — | oil |
| 18-2 | i-Pr | 3-Furyl | A2 | — | oil |
| 18-3 | CFMe₂ | C₆H₅ | A2 | — | oil |
| 18-4 | i-Pr | C₆H₅ | A2 | — | oil |

TABLE 19

| No. | R¹ | —A²—R² | A¹ | (X)ₙ | Physical data |
|---|---|---|---|---|---|
| 19-1 | CH₂-furyl | tetrahydrofuran-2-yl | A2 | 2-OH | |
| 19-2 | CH₂-c-Pr | 4-methyl-tetrahydrofuran-2-yl | " | — | |
| 19-3 | CH₂-cyclopentyl | 5-methyl-tetrahydrofuran-2-yl | " | — | |
| 19-4 | C(H)(CH₃)—C₂H₅ | tetrahydrofuran-2-yl | " | — | |
| 19-5 | CFMe₂ | tetrahydrofuran-2-yl | " | — | oil |
| 19-6 | i-Pr | tetrahydrofuran-2-yl | " | — | oil |

TABLE 20

| No. | R¹ | —A²—R² | A¹ | (X)ₙ | Physical data |
|---|---|---|---|---|---|
| 20-1 | CFMe₂ |  | A2 | — | oil |
| 20-2 | i-Pr |  | A2 | — | oil |

TABLE 21

| No. | R¹ | —A²—R² | A¹ | (X)ₙ | Physical data |
|---|---|---|---|---|---|
| 21-1 | Me |  | A2 | — | |
| 21-2 | CF₃ |  | A2 | — | |
| 21-3 | CHFMe |  | A2 | — | |
| 21-4 | CFMe₂ |  | A2 | — | |
| 21-5 | CClMe₂ |  | A2 | — | |
| 21-6 | CFMe₂ |  | A2 | — | |
| 21-7 | CF₂Cl₃ |  | A2 | — | |

TABLE 22

| No. | R¹ | —A²—R² | A¹ | (X)ₙ | Physical data |
|---|---|---|---|---|---|
| 22-1 | CHClMe | c-Pr | A3 | — | |
| 22-2 | CHClMe | c-Pr | " | — | |
| 22-3 | CHFMe | c-Pr | " | — | oil |
| 22-4 | CF₂CF₃ | c-Pr | " | — | |
| 22-5 | CF₂CHF₂ | c-Pr | " | 3-NO₂ | |
| 22-6 | CF₃ | c-Pr | " | 2,4-Cl₂ | oil |
| 22-7 | CCl₃ | c-Pr | " | — | |
| 22-8 | Me | c-Pr | " | — | oil |
| 22-9 | Et | c-Pr | " | — | oil |
| 22-10 | Pr | c-Pr | " | — | |
| 22-11 | i-Pr | c-Pr | " | — | oil |
| 22-12 | CFMe₂ | c-Pr | " | — | oil |
| 22-13 | C₆H₅ | c-Pr | " | — | |
| 22-14 | CFMe₂ | c-Pr | " | 2-Cl | |
| 22-15 | i-Pr | c-Pr | " | 2-Cl | |
| 22-16 | CFMe₂ | c-Pr | " | 2,4-Cl₂ | |
| 22-17 | i-Pr | c-Pr | " | 2,4-Cl₂ | |
| 22-18 | CFMe₂ | c-Pr | " | 3-Cl | oil |
| 22-19 | i-Pr | c-Pr | " | 3-Cl | |
| 22-20 | i-Pr | c-Pr | " | 3,5-Cl₂ | |
| 22-21 | CFMe₂ | c-Pr | " | 3,5-Cl₂ | |
| 22-22 | CFMe₂ | c-Pr | " | 2-F | |
| 22-23 | CFMe₂ | c-Pr | " | 2-F | |

TABLE 22-continued

| No. | R¹ | —A²—R² | A¹ | (X)ₙ | Physical data |
|---|---|---|---|---|---|
| 22-24 | CFMe₂ | c-Pr | " | 3-F | oil |
| 22-25 | i-Pr | c-Pr | " | 3-F | oil |
| 22-26 | i-Pr | c-Pr | " | 3-Me | oil |
| 22-27 | CFMe₂ | c-Pr | " | 3-Me | oil |
| 22-28 | CFMe₂ | c-Pr | " | 3,5-Me₂ | oil |
| 22-29 | i-Pr | c-Pr | " | 3-OMe | oil |
| 22-30 | CFMe₂ | c-Pr | " | 3-OMe | oil |
| 22-31 | CF₃ | c-Pr | " | — | oil |

TABLE 23

| No. | R¹ | —A²—R² | A¹ | (X)ₙ | Physical data |
|---|---|---|---|---|---|
| 23-1 | CFMe₂ | 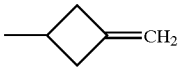 | A3 | — | |
| 23-2 | CClMe₂ | 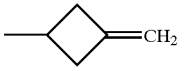 | A3 | — | |
| 23-3 | CHFMe | 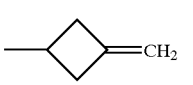 | A3 | — | |

TABLE 24

| No. | R¹ | —A²—R² | A¹ | (X)ₙ | Physical data |
|---|---|---|---|---|---|
| 24-1 | CFMe₂ | 2,2-F₂-c-Pr | A3 | — | |
| 24-2 | i-Pr | " | " | — | |
| 24-3 | CFMe₂ | " | " | 3-Cl | |
| 24-4 | CFMe₂ | " | " | 3,5-Cl₂ | |
| 24-5 | CFMe₂ | " | " | 3-Me | |
| 24-6 | CFMe₂ | " | " | 3-Br | |
| 24-7 | CFMe₂ | " | " | 3-F | |
| 24-8 | CFMe₂ | " | " | 3,5-F₂ | |
| 24-9 | CFMe₂ | " | " | 3-OMe | |
| 24-10 | CFMe₂ | " | " | 3-OH | |

TABLE 25

| No. | R¹ | —A²—R² | A¹ | (X)ₙ | Physical data |
|---|---|---|---|---|---|
| 25-1 | CFMe₂ | 2,2-Cl₂-c-Pr | A3 | — | |
| 25-2 | CFMe₂ | 2,2-Cl₂-c-Pr | A3 | 3-Cl | |

TABLE 26

| No. | R¹ | —A²—R² | A¹ | (X)ₙ | Physical data |
|---|---|---|---|---|---|
| 26-1 | CFMe₂ | 2,2-Me₂-c-Pr | A3 | — | |
| 26-2 | CHMe₂ | " | A3 | — | |
| 26-3 | CFMe₂ | " | A3 | 3-F | |
| 26-4 | CFMe₂ | " | A3 | 3-Me | |
| 26-5 | CFMe₂ | " | A3 | 3-OMe | |
| 26-6 | CFMe₂ | " | A3 | 3-Cl | |

TABLE 27

| No. | R¹ | —A²—R² | A¹ | (X)ₙ | Physical data |
|---|---|---|---|---|---|
| 27-1 | Me | 2,2,3,3-F₄-c-Bu | A3 | — | |
| 27-2 | (CH₂)₄—CH₃ | " | A3 | — | |
| 27-3 | CFMe₂ | " | A3 | — | |

TABLE 28

| No. | R¹ | —A²—R² | A¹ | (X)ₙ | Physical data |
|---|---|---|---|---|---|
| 28-1 | Me | c-Bu | A3 | — | |
| 28-2 | Et | c-Bu | " | — | |
| 28-3 | Pr | c-Bu | " | — | |
| 28-4 | i-Pr | c-Bu | " | — | oil |
| 28-5 | i-Bu | c-Bu | " | — | oil |
| 28-6 | CH₂-i-Pr | c-Bu | " | — | |
| 28-7 | CF₃ | c-Bu | " | — | |
| 28-8 | CH₂F | c-Bu | " | — | |
| 28-9 | CF₂CHF₂ | c-Bu | " | — | |
| 28-10 | CFMe₂ | c-Bu | " | — | oil |
| 28-11 | i-Pr | c-Bu | " | 4-NO₂ | |
| 28-12 | CFMe₂ | c-Bu | " | 2-CF₃ | |
| 28-13 | i-Pr | c-Bu | " | 3-Cl | oil |
| 28-14 | CFMe₂ | c-Bu | " | 3-Cl | oil |
| 28-15 | i-Pr | c-Bu | " | 3-CF₃ | |
| 28-16 | CFMe₂ | c-Bu | " | 3-CF₃ | |
| 28-17 | i-Pr | c-Bu | " | 3-Me | oil |
| 28-18 | CFMe₂ | c-Bu | " | 3-Me | oil |
| 28-18 | i-Pr | c-Bu | " | 3-F | |
| 28-19 | CFMe₂ | c-Bu | " | 3-F | |
| 28-20 | i-Pr | c-Bu | " | 3-OMe | oil |
| 28-21 | CFMe₂ | c-Bu | " | 3-OMe | oil |
| 28-22 | CFMe₂ | c-Bu | —CH₂CHNMe₂— | — | |
| 28-23 | CFMe₂ | c-Bu | —CH₂CHNMe₂— | — | |

TABLE 29

| No. | R¹ | —A²—R² | A¹ | (X)ₙ | Physical data |
|---|---|---|---|---|---|
| 29-1 | CFMe₂ | Ox | A3 | — | |
| 29-2 | i-Pr | Ox | A3 | — | |
| 29-3 | CFMe₂ | Ox | A3 | 3-Cl | |
| 29-4 | c-Pr | Ox | A3 | 3-Cl | |
| 29-5 | CFMe₂ | Ox | A3 | 3,5-Cl₂ | |
| 29-6 | CFMe₂ | Ox | A3 | 3-F | |
| 29-7 | CFMe₂ | Ox | A3 | 3-Me | |
| 29-8 | CFMe₂ | Ox | A3 | 3-OMe | |
| 29-9 | CFMe₂ | Ox | A3 | 3-F | |
| 29-10 | CFMe₂ | Ox | A3 | 3,5-F₂ | |

TABLE 30

| No. | R¹ | —A²—R² | A¹ | (X)ₙ | Physical data |
|---|---|---|---|---|---|
| 30-1 | i-Pr | c-Pr | A4 | — | oil |
| 30-2 | CFMe₂ | c-Pr | A4 | — | oil |
| 30-3 | CFMe₂ | 2,2-Cl₂-c-Pr | A4 | — | |
| 30-4 | CF₃ | 2,2-F₂-c-Pr | A4 | — | |

TABLE 31

| No. | R¹ | —A²—R² | A¹ | (X)ₙ | Physical data |
|---|---|---|---|---|---|
| 31-1 | CFMe₂ | c-Bu | A4 | — | oil |
| 31-2 | CF₃ | c-Bu | A4 | — | |
| 31-3 | i-Pr | c-Bu | A4 | — | oil |

TABLE 32

| No. | R¹ | —A²—R² | A¹ | (X)ₙ | Physical data |
|---|---|---|---|---|---|
| 32-1 | i-Pr | CH₂-c-Pr | A2 | — | oil |
| 32-2 | CFMe₂ | CH₂-c-Pr | " | — | oil |
| 32-3 | i-Pr | CH₂-c-Pr | " | 3-Br | |
| 32-4 | CFMe₂ | CH₂-c-Pr | " | 3-Br | |
| 32-5 | i-Pr | CH₂-c-Pr | " | 3-Cl | oil |
| 32-6 | CFMe₂ | CH₂-c-Pr | " | 3-Cl | oil |
| 32-7 | i-Pr | CH₂-c-Pr | " | 3-F | |
| 32-8 | CFMe₂ | CH₂-c-Pr | " | 3-F | |
| 32-9 | i-Pr | CH₂-c-Pr | " | 3-Me | oil |
| 32-10 | CFMe₂ | CH₂-c-Pr | " | 3-Me | oil |
| 32-11 | i-Pr | CH₂-c-Pr | " | 3-OMe | oil |
| 32-12 | CFMe₂ | CH₂-c-Pr | " | 3-OMe | oil |
| 32-13 | CFMe₂ | CH₂-c-Pr | —CH₂—CHOMe— | — | |
| 32-14 | CF₃ | CH₂-c-Pr | —CH₂—CHOEt— | — | |
| 32-15 | CH₂F | CH₂-c-Pr | —CH₂—CHOAc- | — | |
| 32-16 | CHF₂ | CH₂-c-Pr | —CH₂—CHOMe— | — | |
| 32-17 | CHF₂ | CH₂-c-Pr | —CH₂—CH(OCOEt)— | — | |
| 32-18 | CFMe₂ | CH₂-c-Pr | —CH₂—CHSMe— | 2-Cl | |
| 32-19 | CClMe₂ | CH₂-c-Pr | —CH₂—CHSEt— | 2,5-Cl₂ | |

TABLE 33

| No. | R¹ | —A²—R² | A¹ | (X)ₙ | Physical data |
|---|---|---|---|---|---|
| 33-1 | 3,5-Cl₂—C₆H₃ | CH₂-(2,2-F₂-c-Pr) | A2 | — | |
| 33-2 | CFMe₂ | " | " | — | oil |
| 33-3 | i-Pr | " | " | — | oil |
| 33-4 | Et | " | " | — | |
| 33-5 | CFMe₂ | " | " | 3-Cl | |
| 33-6 | i-Pr | " | " | 3-Cl | |
| 33-7 | CFMe₂ | " | " | 3-OMe | |
| 33-8 | CFMe₂ | " | " | 3-Me | |
| 33-9 | CFMe₂ | " | " | 3-F | |
| 33-10 | CFMe₂ | " | " | 3-I | |
| 33-12 | CFMe₂ | " | " | 3-Br | |
| 33-13 | CFMe₂ | " | " | 3-Cl, 5-F | |

TABLE 34

| No. | R¹ | —A²—R² | A¹ | (X)ₙ | Physical data |
|---|---|---|---|---|---|
| 34-1 | CFMe₂ | CH₂-(2,2-Cl₂-c-Pr) | A2 | | |
| 34-2 | i-Pr | " | " | | |
| 34-3 | CFMe₂ | " | " | 3-F | |
| 34-4 | CF(CF₃)₂ | " | " | 3-F | |
| 34-5 | CFMe₂ | " | " | 3-Cl | |
| 34-6 | CClMe₂ | " | " | 3-Cl | |
| 34-7 | CFMe₂ | " | " | 3-Me | |
| 34-8 | Me | " | " | 3-Me | |

TABLE 35

| No. | R¹ | —A²—R² | A¹ | (X)ₙ | Physical data |
|---|---|---|---|---|---|
| 35-1 | CFMe₂ | CH₂-c-Bu | A2 | — | |
| 35-2 | i-Pr | CH₂-c-Bu | " | — | |
| 35-3 | CH₃ | CH₂-c-Bu | " | — | |
| 35-4 | CF₃ | CH₂-c-Bu | " | — | |
| 35-5 | CClMe₂ | CH₂-c-Bu | " | — | |
| 35-6 | CHFMe | CH₂-c-Bu | " | — | |

TABLE 36

| No. | R¹ | —A²—R² | A¹ | (X)ₙ | Physical data |
|---|---|---|---|---|---|
| 36-1 | CF₂CF₃ | —CHOH-c-Pr | A2 | — | |
| 36-2 | CF₂CHF₂ | —CHOH-c-Pr | " | — | |

TABLE 36-continued

| No. | R¹ | —A²—R² | A¹ | (X)$_n$ | Physical data |
|---|---|---|---|---|---|
| 36-3 | CFCl$_2$ | —CHOH-c-Pr | " | — | |
| 36-4 | CFMe$_2$ | —CHOH-c-Pr | " | — | |
| 36-5 | CFMe$_2$ | —CHOH-c-Pr | " | 3-Cl | |
| 36-7 | i-Pr | —CHOH-c-Bu | " | — | |
| 36-8 | CFMe$_2$ | —CHOH-c-Bu | " | — | |
| 36-9 | Me | —CHOMe-c-Pr | " | — | |
| 36-10 | CF$_3$ | —CHOMe-c-Bu | " | — | |

TABLE 37

| No. | R¹ | —A²—R² | A¹ | (X)$_n$ | Physical data |
|---|---|---|---|---|---|
| 37-1 | CF$_3$ | CH$_2$—Ox | A2 | — | |
| 37-2 | CFMe$_2$ | " | " | — | |
| 37-3 | i-Pr | " | " | — | |

TABLE 38

| No. | R¹ | —A²—R² | A¹ | (X)$_n$ | Physical data |
|---|---|---|---|---|---|
| 38-1 | CH$_2$F | CH$_2$—(oxetane) | A2 | — | |
| 38-2 | CHF$_2$ | CH$_2$—(oxetane) | A2 | — | |
| 38-3 | CClF$_2$ | CH$_2$—(oxetane) | A2 | — | |
| 38-4 | CFMe$_2$ | CH$_2$—(oxetane) | A2 | — | |
| 38-5 | i-Pr | CH$_2$—(oxetane) | A2 | — | |
| 38-6 | CFMe$_2$ | CH$_2$—(oxetane) | A2 | — | |
| 38-7 | CFMe$_2$ | CH$_2$—(3-Me-oxetane) | A2 | — | |
| 38-8 | i-Pr | CH$_2$—(3-Me-oxetane) | A2 | — | |

TABLE 39

| No. | R¹ | —A²—R² | A¹ | (X)$_n$ | Physical data |
|---|---|---|---|---|---|
| 39-1 | C(F)(OMe)—CF$_3$ | CH$_2$-(1,2,4-triazol-1-yl) | A2 | 4-CN | |
| 39-2 | CF(OEt)CF$_3$ | CH$_2$-(1,2,4-triazol-1-yl) | A2 | 3-OCH$_3$ | |
| 39-3 | CFMe$_2$ | CH$_2$-(1,2,4-triazol-1-yl) | A2 | 3-Cl | |
| 39-4 | CFMe$_2$ | CH$_2$-(imidazol-1-yl) | A2 | — | |
| 39-5 | Et | CH$_2$-(imidazol-1-yl) | A2 | — | |

TABLE 40

| No. | R¹ | —A²—R² | A¹ | (X)$_n$ | Physical data |
|---|---|---|---|---|---|
| 40-1 | CFMe$_2$ | CH$_2$—Ox | A3 | 3-Cl | |
| 40-2 | CFMe$_2$ | CH$_2$—Ox | A3 | 3-Me | |
| 40-3 | CFMe$_2$ | CH$_2$—Ox | A3 | 3-CF$_3$ | |
| 40-4 | CFMe$_2$ | CH$_2$—Ox | A3 | 3-F | |

TABLE 41

| No. | R¹ | —A²—R² | A¹ | (X)$_n$ | Physical data |
|---|---|---|---|---|---|
| 41-1 | CHMeEt | CH$_2$—CH$_2$—Ox | A2 | 3,5-F$_2$ | |
| 41-2 | CFMe$_2$ | CH$_2$—CH$_2$Ox | A2 | — | |
| 41-3 | CFMe$_2$ | (CH$_2$)$_2$—c-Pr | A2 | — | |
| 41-4 | c-Pr | (CH$_2$)$_2$—c-Pr | A2 | 2,4-Br$_2$ | |
| 41-5 | CH$_3$ | CH$_2$CHOH—c-Bu | A2 | — | |
| 41-6 | CH$_2$Cl | CH$_2$CHOH—c-Bu | A2 | — | |
| 41-7 | CH$_2$F | CH$_2$CHOCHCH$_2$-(tetrahydrofuran) | A2 | — | |
| 41-8 | CFMe$_2$ | CH$_2$CH$_2$—c-Bu | A2 | — | |
| 41-9 | CFMe$_2$ | CH$_2$-cyclobutenyl | A2 | — | |
| 41-10 | CFMe$_2$ | CH$_2$-cyclobutenyl | A2 | — | |
| 41-11 | CFMe$_2$ | CH$_2$-cyclopentenyl | A2 | — | |
| 41-12 | CFMe$_2$ | CH$_2$-cyclopentenyl | A2 | — | |
| 41-13 | CFMe$_2$ | CH$_2$-cyclopentadienyl | A2 | — | |

TABLE 41-continued

| No. | R¹ | —A²—R² | A¹ | (X)$_n$ | Physical data |
|---|---|---|---|---|---|
| 41-14 | CFMe₂ | (cyclohexenyl) | A2 | — | |
| 41-15 | CFMe₂ | (bicyclic structure) | A2 | — | |
| 41-16 | CFMe₂ | (bicyclic structure) | A2 | — | |
| 41-17 | CFMe₂ | (bicyclic structure) | A2 | — | |
| 41-18 | CFMe₂ | (bicyclic structure) | A2 | — | |

TABLE 42

Compounds of the formula (2)

(2)

| No. | R¹ | —A²—R² | R³ | A¹ | (X)$_n$ | Physical data |
|---|---|---|---|---|---|---|
| 42-1 | Me | Ox | Me | A2 | — | |
| 42-2 | CFMe₂ | c-Pr | Et | A2 | 2,4-Cl₂ | |
| 42-3 | CFMe₂ | c-Pr | i-Pr | A2 | — | |
| 42-4 | i-Pr | c-Bu | NH—Me | A2 | — | |
| 42-5 | i-Pr | c-Bu | NH—Et | A2 | — | |
| 42-6 | Me | CH₂—c-Bu | NMe₂ | A3 | 4-Cn | |
| 42-7 | Et | CH₂—c-Bu | NEt₂ | A3 | 4-Et | |
| 42-8 | Me | c-Bu | H | A3 | 4-i-Pr | |
| 42-9 | Et | c-Bu | H | A3 | 4-c-Pr | |
| 42-10 | CFMe₂ | CH₂—c-Pr | NHAc | A2 | — | |
| 42-11 | CClMe₂ | CH₂—c-Pr | NHCOEt | A2 | — | |
| 42-12 | CH₂—c-Pr | CH₂—c-Bu | NHCOPh | A2 | — | |

TABLE 43

Compounds of the formula (3)

(3)

| No. | R¹ | —A²—R² | R³ | R⁴ | A¹ | (X)$_n$ | Physical data |
|---|---|---|---|---|---|---|---|
| 43-1 | CH(OMe)Me | c-Pentyl | NH₂ | NHAc | A2 | — | |
| 43-2 | CH(OEt)Me | c-Pentyl | NH₂ | NHCHO | A2 | — | |
| 43-3 | CMe₂CN | c-Bu | NH₂ | NHCOEt | A2 | — | |
| 43-4 | CMe₂—SMe | c-Bu | NH₂ | Et | A2 | — | |
| 43-5 | CFMe₂ | c-Bu | NH₂ | Me | A2 | — | |
| 43-6 | CHFMe | c-Pr | NH₂ | n-Pr | A3 | — | |
| 43-7 | CHClMe | c-Pr | NH₂ | n-Bu | A3 | — | |

TABLE 44

Compounds of the formula (4)

(4)

| No. | R¹ | A²—R² | X$_n$ | Z | Physical data |
|---|---|---|---|---|---|
| 44-1 | CFMe₂ | c-Pr | — | H | oil |
| 44-2 | i-Pr | c-Pr | — | H | oil |
| 44-3 | Me | c-Pr | — | H | |
| 44-4 | CFMe₂ | c-Pr | 3-Cl | H | |
| 44-5 | i-Pr | c-Pr | 3-Cl | H | |
| 44-6 | CFMe₂ | c-Pr | 3-CH₃ | H | |
| 44-7 | CFMe₂ | c-Pr | 3-CH₃ | H | |
| 44-8 | CHFMe | c-Pr | — | Br | |
| 44-9 | CFMe₂ | c-Pr | — | Br | |
| 44-10 | i-Pr | c-Pr | — | Br | |
| 44-11 | CFMe₂ | c-Pr | — | Cl | |
| 44-12 | i-Pr | c-Pr | — | Cl | |
| 44-13 | CHFCH₃ | c-Pr | — | Cl | |
| 44-14 | CFMe₂ | c-Bu | — | H | |
| 44-15 | i-Pr | c-Bu | — | H | |
| 44-16 | CFMe₂ | i-Bu | — | Cl | |
| 44-17 | CFMe₂ | c-Bu | — | Br | |
| 44-18 | CHFCH₃ | t-Bu | — | Cl | |
| 44-19 | CHFCH₃ | t-Bu | — | Br | |
| 44-20 | CFMe₂ | c-Pr | — | Me | |
| 44-21 | CH₃ | c-Pr | — | Me | |
| 44-22 | CFMe₂ | c-Bu | — | Me | |

NMR data for individual examples:

Example 4-2

¹H NMR (DMSO-d₆): δ=1.5 (s, 3H), 1.6 (s, 3H), 1.5–2.0 (m), 2.4–2.6 (m), 4.0 (m, 1H), 7.2 (m, 5H)

Example 4-28

¹NMR (CDCl₃): 1.6 (s, 3H), 1.7 (s, 3H), 1.5–1.9 (m), 2.4 (m, 2H), 2.6–2.7 (m, 2H) 4.1 (m, 1H), 4.1 (m, 1H), 6.8–7.0 (m, 3H), 7.2 (m, 1H)

Example 18-1

$^1$H NMR (DMSO-d$_6$): δ=1.5 (s, 3H), 1.6 (s, 3H), 1.7–2.1 (m, 2H), 2.5–2.6 (m, 2H), 5.0 (m, 1H), 7.2–7.7 (m, 8H)

Example 20-1

$^1$H NMR (CDCl$_3$): δ=1.5 (s, 3H), 1.6 (s, 3H), 1.6–2.4 (m, 5H), 2.5–2.8 (m, 2H), 3.6–3.9 (m, 4H), 4.2 m (1H), 7.2 m (5H)

Example 22-3

$^1$H NMR (DMSO-d$_6$): δ=0.1 (m, 1H), 0.3 (m, 2H), 0.4 (m, 1H), 0.9 (m, 1H), 1.5 (s, 3H), 1.6 (s, 3H), 3.5 m (1H), 7.1–7.3 (m, 5H)

Example 22-25

$^1$H NMR (CDCl$_3$): δ=0.2–0.6 (m, 4H), 0.8 (m, 1H), 1.2 (d, 6H), 1.6–1.8 (m, 4H), 2.5–2.7 (m, 2H), 3.5 m (1H), 6.9 (m, 3H), 7.2 m (1H)

Example 28-10

$^1$H NMR (DMSO-d$_6$): δ=1.5 (s, 3H), 1.6 (s, 3H), 1.5–1.9 (m), 2.6 (m), 4.0 (m, 1H), (m, 1H), 7.1–7.3 m (5H)

Example 30-2

$^1$H NMR (CDCl$_3$): δ=0.2–0.6 m (4H), 0.8–1.0 (m, 3H), 1.4 m (2H), 1.5 (s, 3H), 1.7 (s, 3H), 2.6 (t, 2H), 3.5 (m, 1H), 7.1–7.3 (m, 5H)

Example 32-12

$^1$H NMR (DMSO-d$_6$): δ=0.1 (m, 2H), 0.4 (m, 2H), 0.7 m (1H), 1.2 (d, 6H), 1.4 (m, 3H), 1.8 (m, 2H), 2.5–2.7 m (2H), 3.7 (m, 3H), 4.0 (m, 1H), 6.7 (m, 3H), 7.2 m (1H)

Example 33-3

$^1$H NMR (DMSO-d$_6$): δ=1.1 (d, 6H), 1.5–1.9(m), 2.5–2.7 (m), 4.1 (m, 1H), 7.1–7.3 (m, 5H)

Example 44-1

1H NMR (DMSO): δ=0.2–0.6 (4H), 1.0 (m, 1H), 1.5 (m, 3H), 1.6 (m, 3H), 4.1 (m, 1H), 6.3 (dd, 1H), 6.5 (d, 1H), 7.2–7.4 (m, 5H)

B. FORMULATION EXAMPLES a) A dust is obtained by mixing 10 parts by weight of a compound of the formula (I) and 90 parts by weight of talc as inert material and grinding the mixture in a hammer mill.

b) A wettable powder which is readily dispersible in water is obtained by mixing 25 parts by weight of a compound of the formula (I), 64 parts by weight of kaolin-containing quartz as inert material, 10 parts by weight of potassium lignosulfonate and 1 part by weight of sodium oleoylm-ethyltaurinate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol,polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing
   75 parts by weight of a compound of the formula (I),
   10 " " of calcium ligno-sulfonate,
   5 " " of sodium laurylsulfate,
   3 " " of polyvinyl alcohol and
   7 " " of kaolin,
   grinding the mixture in a pinned disk mill and granulating the powder in a fluidized bed by spraying on water as granulation liquid.

f) Alternatively, water-dispersible granules are obtained by homogenizing and precomminuting, on a colloid mill,
   25 parts by weight of a compound of the formula (I),
   5 " " of sodium 2,2'-dinaphthylmethane-6,6'-disulfonate,
   2 " " of sodium oleoylmethyltaurinate,
   1 part by weight of polyvinyl alcohol,
   17 parts by weight of calcium carbonate and
   50 " " of water,
   subsequently grinding the mixture on a bead mill and atomizing and drying the resulting suspension in a spray tower by means of a single-substance nozzle.

C. BIOLOGICAL EXAMPLES

1 Pre-emergence Effect on Weeds

Seeds or rhizome pieces of monocotyledonous and dicotyledonous weeds plants are placed in sandy loam soil in plastic pots and covered with soil. The compounds according to the invention which are formulated in the form of wettable powders or emulsion concentrates are then applied to the surface of the soil cover in the form of an aqueous suspension or emulsion at an application rate of 600 to 800 l of water/ha (converted), in various dosages.

After the treatment, the pots are placed in the greenhouse and kept under good growth conditions for the weeds. After the test plants have emerged, the damage to the plants or the negative effect on the emergence is scored visually after a test period of 3 to 4 weeks by comparison with untreated controls. As shown by the test results, the compounds according to the invention have a good herbicidal pre-emergence action against a broad range of grass weeds and dicotyledonous weeds. For example, Example Nos. 4-1, 4-2, 4-3, 4-10, 4-11, 4-14, 4-15, 4-23, 4-24, 4-25, 4-26, 4-27, 4-28, 4-29, 8-1, 8-2, 9-1, 9-2, 9-3, 9-4, 9-5, 9-6, 9-7, 9-8, 9-9, 9-10, 9-11, 9-12, 9-13, 9-14, 9-15, 9-16, 9-17, 9-18, 9-19, 10-1, 18-1, 18-2, 18-3, 18-4, 19-5, 19-6, 20-1, 20-2, 22-3, 22-6, 22-8, 22-9, 22-11, 22-12, 22-18, 22-24, 22-25, 22-26, 22-27, 22-28, 22-29, 22-30, 33-31, 28-4, 28-5, 28-10, 28-13, 28-14, 28-17, 28-18, 28-20, 28-21, 30-1, 30-2, 31-1, 31-2, 31-3, 32-1, 32-2, 32-5, 32-6, 32-9, 32-10, 32-11, 32-12, 33-2, 33-4, 44-1 and 44-2 (see Tables 1 to 44) show action in the test against harmful plants such as *Stellaria media, Lolium multiflorum, Amaranthus retroflexus, Sinapis alba, Avena sativa* and *Setaria viridis* when applied pre-emergence at an application rate of 1 kg or less of active substance per hectare.

2. Post-emergence Effect on Weeds

Seeds or rhizome pieces of monocotyledonous and dicotyledonous weeds are placed in sandy loam soil in plastic pots, covered with soil and grown in the greenhouse under good growth conditions. Three weeks after sowing, the test plants are treated in the three-leaf stage. The compounds according to the invention which are formulated as wettable powders or as emulsion concentrates are sprayed in various dosages on the green parts of the plants at an application rate of 600 to 800 l of water/ha (converted). After the test plants have remained in the greenhouse for about 3 to 4 weeks under ideal growth conditions, the effect of the preparations is scored visually by comparison with untreated controls. The agents according to the invention also have a good herbicidal post-emergence action against a broad range of economically important grass weeds and dicotyledonous weeds. For example, Example Nos. 4-1, 4-2, 4-3, 4-10, 4-11, 4-14, 4-15, 4-23, 4-24, 4-25, 4-26, 4-27, 4-28, 4-29, 8-1, 8-2, 9-1, 9-2, 9-3, 9-4, 9-5, 9-6, 9-7, 9-8, 9-9, 9-10, 9-11, 9-12, 9-13, 9-14, 9-15, 9-16, 9-17, 9-18, 9-19, 10-1, 18-1, 18-2, 18-3, 18-4, 19-5, 19-6, 20-1, 20-2, 22-3, 22-6, 22-8, 22-9, 22-11, 22-12, 22-18, 22-24, 22-25, 22-26, 22-27, 22-28, 22-29, 22-30, 33-31, 28-4, 28-5, 28-10, 28-13, 28-14, 28-17, 28-18, 28-20, 28-21, 30-1, 30-2, 31-1, 31-2, 31-3, 32-1, 32-2, 32-5, 32-6, 32-9, 32-10, 32-11, 32-12, 33-2, 33-4, 44-1 and 44-2 (see Tables 1 to 43) show, in the test, a very good herbicidal action against harmful plants such as *Sinapis alba, Echinochloa crus-galli, Lolium multiflorum, Stellaria media, Cyperus iria, Amaranthus retroflexus, Setaria viridis* and *Avena sativa* when applied post-emergence at an application rate of 1 kg and less of active substance per hectare.

3. Effect on Harmful Plants in Rice

Transplanted and seeded rice and typical broad-leaved and monocotyledonous rice weeds are grown in the greenhouse to the three-leaf stage (*Echinochloa crus- galli* 1.5 leaf) under paddy rice conditions (depth of the water: 2–3 cm) in sealed plastic pots. They are then treated with the compounds according to the invention. To this end, the formulated active substances are suspended, dissolved or emulsified in water and applied in various dosages by pouring into the water with which the test plants are flooded. After this treatment, the test plants are placed in the greenhouse under ideal growth conditions and kept thus over the entire experimental period.

Approximately three weeks after application, the test is evalued by means of visually scoring the damage to the plants by comparison with untreated controls. The compounds according to the invention have a very good herbicidal action against harmful plants. For example, the compounds of Example Nos. 4-1, 4-2, 4-14, 4-15, 4-23, 4-24, 9-4, 9-5, 9-9, 9-7 and 9-10 (see Tables 1 to 44) show, in the test, a very good herbicidal action against harmful plants which are typical for rice cultivation, such as, for example, *Cyperus monti, Echinochloa crus-galli* and *Sagittaria pygmaea*.

4 Tolerance by Crop Plants

In further greenhouse experiments, seeds of a substantial number of crop plants and weeds are placed in sandy loam soil and covered with soil. Some of the pots are treated immediately as described in Section 1, and the remaining pots are placed in a greenhouse until the plants have developed two to three true leaves and then sprayed with various dosages of the substances of the formula (I) according to the invention, as described in Section 2. Visual scoring four to five weeks after the application and after the plants have been in the greenhouse reveal that the compounds according to the invention do not inflict any damage on dicotyledonous crops such as, for example, soya, cotton, oilseed rape, sugar beet and potatoes when used pre- and post-emergence, even when high dosages of active substance are used. Moreover, some substances also leave Gramineae crops such as, for example, barley, wheat, rye, sorghum, maize or rice unharmed. Some of the compounds of the formula (I) have a high selectivity and are therefore suitable for controlling undesired plant growth in agricultural crops.

What is claimed is:
1. A compound of the formula (I) or a salt thereof

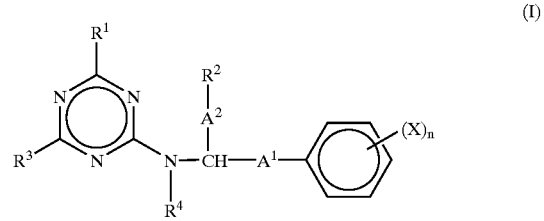

(I)

in which
$R^1$ is aryl which is unsubstituted or substituted, or $(C_3–C_9)$cycloalkyl which is unsubstituted or substituted, or heterocyclyl which is substituted or unsubstituted, or $(C_1–C_6)$alkyl, $(C_2–C_6)$alkenyl or $(C_2–C_6)$alkynyl,
each of the last-mentioned 3 radicals being unsubstituted or substituted by one or more radicals selected from the group consisting of halogen, hydroxyl, cyano, nitro, thiocyanato, $(C_1–C_4)$alkoxy, $(C_1–C_4)$haloalkoxy, $(C_2–C_4)$alkenyloxy, $(C_2–C_4)$haloalkenyloxy, $(C_1–C_4)$alkylthio, $(C_1–C_4)$alkylsulfinyl, $(C_1–C_4)$alkylsulfonyl, $(C_1–C_4)$haloalkylsulfinyl, $(C_1–C_4)$haloalkylsulfonyl and $(C_3–C_9)$cycloalkyl which is unsubstituted or substituted, and phenyl which is unsubstituted or substituted, and heterocyclyl which is unsubstituted or substituted, and radicals of the formulae R'—C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"N—C(=Z')—NR'"— in which R', R" and R'" in each case independently of one another are $(C_1–C_6)$alkyl, aryl, aryl-$(C_1–C_6)$alkyl, $(C_3–C_9)$cycloalkyl or $(C_3–C_9)$cycloalkyl-$(C_1–C_6)$alkyl, each of the 5 last-mentioned radicals being unsubstituted or substituted, and in which Z and Z' independently of one another are in each case an oxygen or sulfur atom,
$R^1$ is cyclopropyl, cyclobutyl, cyclopentyl or cyclohexyl, each of the last-mentioned four radicals being unsubstituted or substituted, or is $(C_4–C_9)$cycloalkenyl which is unsubstituted or substituted, or is heterocyclyl which is unsubstituted or substituted,
$R^3$ is hydrogen, $(C_1–C_6)$alkyl, aryl or $(C_3–C_9)$cycloalkyl, each of the last-mentioned 3 radicals being unsubstituted or substituted, or a radical of the formula —N($B^1$-$D^1$)($B^2$-$D^2$) or —NR$^1$—N($B^1$-$D^1$)($B^2$-$D^2$) in which $B^1$, $B^2$, $D^1$ and $D^2$ are in each case as defined below and $R^1$=hydrogen, $(C_1–C_6)$alkyl or $((C_1–C_4)$alkyl)carbonyl,
$R^4$ is a radical of the formula -$B^3$-$D^3$, $B^3$ and $D^3$ being as defined below,
$A^1$ is straight-chain alkylene having 1 to 5 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^4$-$D^4$, $B^4$ and $D^4$ being as defined below,
$A^2$ is a direct bond or straight-chain alkylene having 1 to 4 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^5$-$D^5$ or a divalent radical of the formula $V^1$, $V^2$, $V^3$, $V^4$ or $V^5$,

—$CR^6R^7$—$W^*$—$CR^8R^9$—     (V¹)

—$CR^{10}R^{11}$—$W^*$—$CR^{12}R^{13}$—$CR^{14}R^{15}$—     (V²)

—$CR^{16}R^{17}$—$CR^{18}R^{19}$—$W^*$—$CR^{20}R^{21}$—     (V³)

—$CR^{22}R^{23}$—$CR^{24}R^{25}$—$W^*$—     (V⁴)

—$CR^{26}R^{27}$—$W^*$     (V⁵)

each of the radicals $R^6$ to $R^{27}$ in each case independently of one another being hydrogen, halogen, nitro, cyano, thiocyanato or a radical of the formula -$B^6$-$D^6$, $W^*$ is in each case an oxygen atom, a sulfur atom or a group of the formula —NH— or —N(CH₃)—, and $B^5$, $B^6$, $B^7$, $D^5$ and $D^6$ are as defined below, $B^1$, $B^2$ and $B^3$ in each case independently of one another are a direct bond or a divalent group of the formulae —C50 $Z^*$)—, —C(=$Z^*$)—$Z^{**}$—, —C(=$Z^*$)—NH— or —C(=$Z^*$)$NR^*$ , $Z^*$ being an oxygen or sulfur atom, $Z^{**}$ an oxygen or sulfur atom and $R^*$ ($C_1$–$C_6$)alkyl, aryl, aryl-($C_1$–$C_6$)alkyl, ($C_3$–$C_9$)cycloalkyl or ($C_3$–$C_9$)cycloalkyl-($C_1$–$C_6$)alkyl, each of the 5 last-mentioned radicals being unsubstituted or substituted, $B^4$, $B^5$ and $B^6$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —$NR^o$—, —O—$NR^o$—, —$NR^o$—O—, —$NR^o$—CO—, —CO—$NR^o$—, —O—CO—$NR^o$— or —$NR^o$—CO—O—, p being the integer 0, 1 or 2 and $R^o$ being hydrogen, ($C_1$–$C_6$)alkyl, aryl, aryl-($C_1$–$C_6$)alkyl, ($C_3$–$C_9$)cycloalkyl or ($C_3$–$C_9$)cycloalkyl-($C_1$–$C_6$)alkyl, each of the 5 last-mentioned radicals being unsubstituted or substituted, $D^1$, $D^2$, $D^3$, $D^4$, $D^5$ and $D^6$ in each case independently of one another are hydrogen, ($C_1$–$C_6$)alkyl, aryl, aryl-($C_1$–$C_6$)alkyl, ($C_3$–$C_9$)cycloalkyl or ($C_3$–$C_9$)cycloalkyl-($C_1$–$C_6$)alkyl, each of the 5 last-mentioned radicals being unsubstituted or substituted, or in each case two radicals $D^5$ of two groups -$B^5$-$D^5$ which are bonded to a carbon atom are linked to each other and form an alkylene group having 2 to 4 carbon atoms, this alkylene group being unsubstituted or substituted by one or more radicals selected from the group consisting of ($C_1$–$C_4$)alkyl and ($C_1$–$C_4$)alkoxy, $(X)_n$ is n substituents X, where the X in each case independently of one another are halogen, hydroxyl, amino, nitro, formyl, carboxyl, cyano, thiocyanato, aminocarbonyl or ($C_1$–$C_6$)alkyl, ($C_1$–$C_6$)alkoxy, ($C_1$–$C_6$)alkylthio, mono($C_1$–$C_6$)alkylamino, di($C_1$–$C_4$)alkylamino, ($C_2$–$C_6$)alkenyl, ($C_2$–$C_6$)alkynyl, (($C_1$–$C_6$)alkyl)carbonyl, (($C_1$–$C_6$)alkoxy)carbonyl, mono($C_1$–$C_6$)alkylaminocarbonyl, di($C_1$–$C_4$)alkylaminocarbonyl, N—($C_1$–$C_6$)alkanoylamino or N—($C_1$–$C_4$)alkanoyl—N—($C_1$–$C_4$)alkylamino, each of the last-mentioned 13 radicals being unsubstituted or substituted, or two adjacent radicals X together are a fused cycle which has 4 to 6 ring atoms and is carbocyclic or which contains hetero ring atoms selected from the group consisting of O, S and N and which is unsubstituted or substituted by one or more radicals selected from the group consisting of halogen, ($C_1$–$C_4$)alkyl and oxo, n is 0, 1, 3, 4 or 5, and wherein heterocyclyl in the abovementioned radicals independently of one another is in each case a heterocyclic radical having 3 to 7 ring atoms and 1 to 3 heteroatoms selected from the group consisting of N, O, and S, wherein the total of the carbon atoms in the radicals $A^1$ and $A^2$—$R^2$ amount to at least 6 carbon atoms.

2. A compound of the formula (I) or a salt thereof as claimed in claim 1, wherein $R^1$ is phenyl which is unsubstituted or substituted by one or more radicals selected from the group consisting of halogen, hydroxyl, amino, nitro, formyl, carboxyl, sulfo, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, (($C_1$–$C_4$)alkyl)carbonyl, (($C_1$–$C_4$)alkoxy)carbonyl, aminocarbonyl, mono($C_1$–$C_4$)alkylaminocarbonyl, di($C_1$–$C_4$)alkylaminocarbonyl, ($C_1$–$C_4$)alkylsulfonyl and ($C_1$–$C_4$)haloalkylsulfonyl, or ($C_3$–$C_9$)cycloalkyl which is unsubstituted or substituted by one or more radicals selected from the group consisting of halogen, hydroxyl, amino, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$)alkylthio, ($C_1$–$C_4$)haloalkylthio, mono($C_1$–$C_4$)alkylamino and di($C_1$–$C_4$)alkylamino, or heterocyclyl which is unsubstituted or substituted by one or more radicals selected from the group consisting of halogen, hydroxyl, amino, nitro, formyl, carboxyl, sulfonyl, cyano, thiocyanato, ($C_1$–$C_4$) alkyl, ($C_1$–$C_4$)haloalkyl, ($C_1$–$C_4$)alkoxy, ($C_1$–$C_4$) haloalkoxy, ($C_1$–$C_4$)alkylthio, ($C_1$–$C_4$)haloalkylthio, mono($C_1$–$C_4$)alkylamino, di($C_1$–$C_4$)alkylamino, ($C_3$–$C_9$)cycloalkyl, (($C_1$–$C_4$)alkyl)carbonyl, (($C_1$–$C_4$)alkoxy)carbonyl, aminocarbonyl, mono ($C_1$–$C_4$)alkylaminocarbonyl, di($C_1$–$C_4$) alkylaminocarbonyl, ($C_1$–$C_4$)alkylsulfonyl and ($C_1$–$C_4$)haloalkylsulfonyl, or ($C_1$–$C_6$)alkyl, ($C_2$–$C_6$)alkenyl or ($C_2$–$C_6$)alkynyl, each of the last-mentioned 3 radicals being unsubstituted or substituted by one or more radicals selected from the group consisting of halogen, hydroxyl, cyano, nitro, thiocyanato, ($C_1$–$C_4$)alkoxy, ($C_1$–$C_4$) haloalkoxy, ($C_2$–$C_4$)alkenyloxy, ($C_2$–$C_4$) haloalkenyloxy, ($C_1$–$C_4$)alkylthio, ($C_1$–$C_4$) alkylsulfinyl, ($C_1$–$C_4$)alkylsulfonyl, ($C_1$–$C_4$) haloalkylsulfinyl, ($C_1$–$C_4$)haloalkylsulfonyl and ($C_3$–$C_6$)cycloalkyl which is unsubstituted or substituted by one or more radicals selected from the group consisting of halogen, hydroxyl, amino, cyano, thiocyanato, ($C_1$–$C_4$)alkyl, ($C_1$–$C_4$)haloalkyl, ($C_1$–$C_4$)alkoxy, ($C_1$–$C_4$)haloalkoxy, ($C_1$–$C_4$) alkylthio, ($C_1$–$C_4$)haloalkylthio, mono($C_1$–$C_4$) alkylamino and di($C_1$–$C_4$)alkylamino, and phenyl and heterocyclyl, each of the two last-mentioned radicals being unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $((C_1-C_4)$alkyl)carbonyl, $((C_1-C_4)$alkoxy)carbonyl, aminocarbonyl, mono$(C_1-C_4)$alkylamino-carbonyl, di$(C_1-C_4)$alkylaminocarbonyl, $(C_1-C_4)$alkylsulfonyl and $(C_1-C_4)$haloalkylsulfonyl, and radicals of the formulae R'C(=Z')—, R'—C(=Z')—Z—, R'—Z—C(=Z')—, R'R"N—C(=Z')—, R'—Z—C(=Z')—O—, R'R"N—C(=Z')—Z—, R'—Z—C(=Z')—NR"— and R'R"—N—C(=Z')—NR'"— in which R'R" and R'" in each case independently of one another are $(C_1-C_4)$ alkyl, phenyl, phenyl-$(C_1-C_4)$alkyl, $(C_3-C_6)$cycloalkyl or $(C_3-C_6)$cycloalkyl-$(C_1-C_4)$alkyl, each of the 5 last-mentioned radicals being unsubstituted or substituted by one or more radicals selected from the group consisting of halogen, hydroxyl, amino, nitro, formyl, cyano, thiocyanato, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, $(C_3-C_6)$cycloalkyl and in the case of cyclic radicals also $(C_1-C_4)$alkyl and $(C_1-C_4)$haloalkyl, and in which Z and Z' independently of one another are in each case an oxygen or sulfur atom.

3. A compound of the formula (I) or a salt thereof as claimed in claim 1, where $R^2$ is cyclopropyl, cyclobutyl, cyclopentyl cyclohexyl, each of the last-mentioned four radicals being unsubstituted or substituted by one or more radicals selected from the group consisting of the radicals A), B), C) and D), where Group A) is a radical selected from the group consisting of halogen, hydroxyl, amino, nitro, formyl, carboxyl, aminocarbonyl, sulfo, cyano, thiocyanato and oxo, Group B) is a radical selected from the group consisting of $(C_1-C_6)$alkyl, $(C_1-C_6)$alkoxy, $(C_1-C_6)$alkylthio, mono$(C_1-C_6)$alkylamino, di$(C_1-C_4)$alkylamino, $(C_2-C_6)$alkenyl, $(C_2-C_6)$alkynyl, $(C_3-C_9)$cycloalkyl, $(C_4-C_9)$cycloalkenyl, $(C_1-C_6)$alkylidene, $(C_4-C_9)$cycloalkylidene, radicals of the formulae R'—C(=Z')—, R'—C(=Z')—Z—, R'—Z—C(=Z')—, R'R"N—C (=Z')—, R'—Z—C (=Z')—O—, R'R"N—C (=Z')—Z—, R'—Z—C (=Z')—NR" and R'R"N—C(=Z')—NR'"— where R', R" and R'" in each case independently of one another are $(C_1-C_6)$ alkyl, phenyl, phenyl-$(C_1-C_6)$alkyl, $(C_3-C_9)$cycloalkyl or $(C_3-C_9)$cycloalkyl-$(C_1-C_6)$alkyl and where Z and Z' independently of one another are in each case an oxygen or sulfur atom, Group C) is a radical selected from the group consisting of group B), wherein each radical is substituted by one or more radicals selected from the group consisting of halogen, hydroxyl, amino, nitro, formyl, carboxyl, sulfo, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $(C_4-C_9)$cycloalkylene, $(C_4-C_9)$cycloalkylidene, $((C_1-C_4)$alkyl)carbonyl, $((C_1-C_4)$alkoxy)carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, and each of the last-mentioned 21 radicals being unsubstituted or substituted by one or more radicals selected from the group consisting of halogen, nitro, cyano, $(C_1-C_4)$alkoxy, $(C_1-C_4)$alkylthio, $(C_1-C_4)$haloalkoxy, formyl, $(C_1-C_4)$alkylcarbonyl and $(C_1-C_4)$alkoxycarbonyl and, in the case of cyclic radicals, also $(C_1-C_4)$alkyl, $(C_1-C_4)$haloalkyl and $(C_1-C_6)$alkylidene, and where, in the case of cyclic radicals, also $(C_1-C_6)$alkyl, $(C_1-C_6)$haloalkyl and $(C_1-C_6)$alkylidene, and Group D) is selected from the group consisting of divalent or trivalent aliphatic bridges having 1 to 6 carbon atoms which, in the case of divalent bridges, connect two and in the case of trivalent bridges three carbon atoms of the cyclic skeleton and the radical $R^2$ thus represents the radical of a bicycle or tricycle, each of the bridges being unsubstituted or substituted by one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl, $(C_1-C_4)$alkoxycarbonyl and oxo, or $(C_4-C_9)$cycloalkenyl which is unsubstituted or substituted by one or more radicals selected from the group consisting of the radicals A), B), C) and D) as they are defined as radicals for $R^2=(C_3-C_9)$cycloalkyl, or heterocyclyl which is unsubstituted or substituted by one or more radicals selected from the group consisting of the radicals A), B), C) and D) as they are defined as radicals for $R^2=(C_3-C_9)$cycloalkyl.

4. A compound of the formula (I) or a salt thereof as claimed in claim 1, wherein $R^3$ is hydrogen, $(C_1-C_4)$alkyl which is unsubstituted or substituted by one or more radicals selected from the group consisting of halogen, hydroxyl, amino, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino and di$(C_1-C_4)$alkylamino, or phenyl or $(C_3-C_6)$cycloalkyl, each of the last-mentioned 2 radicals being unsubstituted or substituted by one or more radicals selected from the group consisting of halogen, hydroxyl, amino, nitro, formyl, carboxyl, sulfonyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $((C_1-C_4)$alkyl)carbonyl, $((C_1-C_4)$alkoxy)carbonyl, aminocarbonyl, mono$(C_1-C_4)$alkylamino-carbonyl, di$(C_1-C_4)$alkylaminocarbonyl, $(C_1-C_4)$alkylsulfonyl and $(C_1-C_4)$haloalkylsulfonyl, or a radical of the formula $N(B^1-D^1)(B^2-D^2)$, $R^4$ is a radical of the formula $-B^3-D^3$, $A^1$ is straight-chain alkylene having 1 to 5 carbon atoms or straight-chain alkenylene or alkynylene, each of which having 2 to 5 carbon atoms, each of the three last-mentioned divalent radicals being unsubstituted or substituted by one or more radicals selected from the group consisting of halogen, nitro, cyano, thiocyanato and a radical of the formula $-B^4-D^4$, $B^4$ is a direct bond or a divalent group of the formulae —O—, —SO$_2$—, —CO—, —O—CO—, —NR$^o$—, —NR$^o$—CO—, —CO—NR$^o$—, —O—CO—NR$^o$— or —NR$^o$—CO—O—, where $R^o$ and $D^4$ independently of one another are in each case hydrogen, $(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, each of the last-mentioned 5 radicals being unsubstituted or substituted by one or more radicals selected from the group consisting of halogen, hydroxyl, amino, nitro, formyl, carboxyl, sulfonyl, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, $((C_1-C_4)$alkyl)carbonyl, $((C_1-C_4)$alkoxy)carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and in the case of cyclic radicals also $(C_1-C_4)$alkyl and $(C_1-C_4)$haloalkyl, $A^2$ is a direct bond or a group of the formula —$CH_2$—, —$CH_2CH_2$—, —$CH_2CH_2CH_2$— or —$CH_2CH_2CH_2CH_2$, each of the 4 last-mentioned divalent radicals being unsubstituted or substituted by one or more radicals selected from the group consisting of halogen, nitro, cyano, thiocyanato and radicals of the formula -$B^5$-$D^5$, or a divalent radical of the formula $V^1$, $V^2$, $V^3$, $V^4$ or $V^5$,

 (V$^1$)

 (V$^2$)

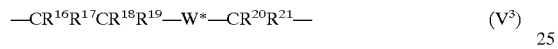 (V$^3$)

 (V$^4$)

 (V$^5$)

where each of the radicals $R^6$ to $R^{27}$ in each case independently of one another is hydrogen, halogen, nitro, cyano, thiocyanato or a radical of the formula -$B^6$-$D^6$, W* is in each case O, S or a group of the formula —NH— or —N(CH$_3$)—, $B^1$, $B^2$ and $B^3$ independently of one another are a direct bond or a divalent group of the formulae —C(=Z*)—, —C(=Z*)—Z**—, —C(=Z*)—NH— or —C(=Z*)—NR*—, where Z*=O or S, Z**=O or S and R*=$(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, each of the 5 last mentioned radicals being unsubstituted or substituted by one or more radicals selected from the group consisting of halogen, hydroxyl, amino, nitro, formyl, carboxyl, sulfo, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $((C_1-C_4)$alkyl)carbonyl, $((C_1-C_4)$alkoxy)carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and in the case of cyclic radicals also $(C_1-C_4)$alkyl and $(C_1-C_4)$haloalkyl;

$B^4$, $B^5$ and $B^6$ independently of one another are a direct bond or a divalent group of the formulae —O—, —S(O)$_p$—, —S(O)$_p$—O—, —O—S(O)$_p$, —CO—, —O—CO—, —CO—O—, —S—CO—, —CO—S—, —S—CS—, —CS—S—, —O—CO—O—, —NR$^o$—, —O—NR$^o$—, —NR$^o$—O—, —NR$^o$—CO—, —CO—NR$^o$—, —O—CO—NR$^o$— or —NR$^o$—CO—O—, where p is the integer 0, 1 or 2 and R$^o$=hydrogen, $(C_1-C_4)$alkyl, phenyl, phenyl-$(C_1-C_4)$alkyl, $(C_3-C_6)$cycloalkyl or $(C_3-C_6)$cycloalkyl-$(C_1-C_4)$alkyl, each of the 5 last-mentioned radicals being unsubstituted or substituted by one or more radicals selected from the group consisting of halogen, hydroxyl, amino, nitro, formyl, carboxyl, sulfo, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $((C_1-C_4)$alkyl)carbonyl, $((C_1-C_4)$alkoxy)carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and in the case of cyclic radicals also $(C_1-C_4)$alkyl and $(C_1-C_4)$haloalkyl, $D^1$, $D^2$, $D^3$, $D^4$, $D^5$ and $D^6$ independently of one another are hydrogen, $(C_1-C_6)$alkyl, phenyl, phenyl-$(C_1-C_4)$alkyl, $(C_3-C_6)$cycloalkyl or $(C_3-C_6)$cycloalkyl-$(C_1-C_6)$alkyl, each of the 5 last-mentioned radicals being unsubstituted or substituted by one or more radicals selected from the group consisting of halogen, hydroxyl, amino, nitro, formyl, carboxyl, sulfo, cyano, thiocyanato, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_9)$cycloalkyl, $((C_1-C_4)$alkyl)carbonyl, $((C_1-C_4)$alkoxy)carbonyl, aminocarbonyl, mono$(C_1-C_4)$alkylaminocarbonyl, di$(C_1-C_4)$alkylaminocarbonyl, $(C_1-C_4)$alkylsulfonyl, $(C_1-C_4)$haloalkylsulfonyl and in the case of cyclic radicals also $(C_1-C_4)$alkyl and $(C_1-C_4)$haloalkyl, $(X)_n$ is n substituents X, where the X independently of one another are halogen, hydroxyl, amino, nitro, formyl, carboxyl, cyano, thiocyanato, aminocarbonyl or $(C_1-C_4)$alkyl, $(C_1-C_4)$alkoxy, $(C_1-C_4)$alkylthio, mono$(C_1-C_4)$alkylamino, di$(C_1-C_4)$alkylamino, $(C_2-C_4)$alkenyl, $(C_2-C_4)$alkynyl, $((C_1-C_4)$alkyl)carbonyl, $((C_1-C_4)$alkoxy)carbonyl, mono$(C_1-C_4)$alkylaminocarbonyl, di$(C_1-C_4)$alkylaminocarbonyl, N—$(C_1-C_6)$alkanoylamino or N—$(C_1-C_4)$alkanoyl-N—$(C_1-C_4)$alkylamino, each of the last-mentioned 13 radicals being unsubstituted or substituted by one or more radicals selected from the group consisting of halogen, hydroxyl, amino, cyano, thiocyanato, $(C_1-C_4)$alkoxy, $(C_1-C_4)$haloalkoxy, $(C_1-C_4)$alkylthio, mono$(C_1-C_4)$alkylamino, di$(C_1-C_4)$alkylamino, $(C_3-C_6)$cycloalkyl, $(C_3-C_6)$cycloalkylamino, $((C_1-C_4)$alkyl)carbonyl, $((C_1-C_4)$alkoxy)carbonyl, aminocarbonyl, mono$(C_1-C_4)$alkylaminocarbonyl, di$(C_1-C_4)$alkylaminocarbonyl, phenyl, phenoxy, phenylthio, phenylcarbonyl, heterocyclyl, heterocyclyloxy, heterocyclylthio and heterocyclylamino, each of the last-mentioned 8 radicals being unsubstituted or having one or more substituents selected from the group consisting of halogen, nitro, cyano, $(C_1-C_4)$alkyl, $(C_1-C_4)$alkoxy, $(C_1-C_4)$alkylthio, $(C_1-C_4)$haloalkyl, $(C_1-C_4)$haloalkoxy, formyl, $(C_1-C_4)$alkylcarbonyl and $(C_1-C_4)$alkoxycarbonyl, or $(C_3-C_9)$cycloalkyl, phenyl, phenoxy, phenylthio, phenylcarbonyl, heterocyclyl, heterocyclyloxy, heterocyclylthio or heterocyclylamino, each of the last-mentioned 9 radicals being unsubstituted or substituted by one or more radicals selected from the group consisting of halogen, hydroxyl, amino, nitro, formyl, carboxyl, cyano, thiocyanato, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, mono$(C_1-C_4)$alkylamino, di$(C_1-C_4)$alkylamino, $(C_3-C_6)$cycloalkyl, $((C_1-C_4)$alkyl)carbonyl, $((C_1-C_4)$alkoxy)carbonyl, aminocarbonyl, mono$(C_1-C_4)$alkylaminocarbonyl and di$(C_1-C_4)$alkylaminocarbonyl, or two adjacent radicals X together are a fused cycle which has 4 to 6 ring atoms and is carbocyclic or contains hetero ring atoms selected from the group consisting of O, S and N and which is unsubstituted or substituted by one or more radicals selected from the group consisting of halogen, $(C_1–C_4)$alkyl and oxo, and n is 0, 1, 2 or 3.

5. A compound of the formula (I) or a salt thereof as claimed in claim 1, wherein $R^2$ is cyclopropyl, cyclobutyl, cyclopentyl or cyclohexyl, each of the latter four radicals being unsubstituted or substituted by one or more radicals selected from the group consisting of halogen, hydroxyl, cyano, thiocyanato, $(C_1–C_4)$alkyl, $(C_1–C_4)$haloalkyl, $(C_1–C_4)$alkoxy, $(C_1–C_4)$haloalkoxy, $(C_1–C_4)$alkylthio, $(C_1–C_4)$haloalkylthio, $(C_1–C_4)$alkylidene, mono$(C_1–C_4)$alkylamino and di$(C_1–C_4)$alkylamino, or heterocyclyl, the last-mentioned radical being unsubstituted or substituted by one or more radicals selected from the group consisting of halogen, hydroxyl, atuino, nitro, formyl, carboxyl, sulfonyl, cyano, thiocyanato, $(C_1–C_4)$alkyl, $(C_1–C_4)$haloalkyl, $(C_1–C_4)$alkoxy, $(C_1–C_4)$haloalkoxy, $(C_1–C_4)$alkylthio, $(C_1–C_4)$haloalkylthio, mono$(C_1–C_4)$alkylamino, di$(C_1–C_4)$alkylamino, $(C_3–C_6)$cycloalkyl, heterocyclyl having 3 to 6 ring atoms, $((C_1–C_4)$alkyl)carbonyl, $((C_1–C_4)$alkoxy)carbonyl, aminocarbonyl, mono$(C_1–C_4)$alkylaminocarbonyl, di$(C_1–C_4)$alkylaminocarbonyl, $(C_1–C_4)$alkylsulfonyl and $(C_1–C_4)$haloalkylsulfonyl.

6. A compound of the formula (I) or a salt thereof as claimed in claim 1, wherein $A^1$ is a radical of the formula —$CH_2$—, —$CH_2CH_2$—, —$CH_2CH_2CH_2$—, —$CH_2CH_2CH_2CH_2$— or —$CH_2CH_2CH_2CH_2CH_2$— and $A^2$ is a direct bond or a group of the formula —$CH_2$—, —$CH_2CH_2$—, —$CH_2CH_2CH_2$—, —$CH_2CH_2CH_2CH_2$—, —$CH_2$—O—$CH_2$—, —$CH_2$—O—$CH_2CH_2$—, —$CH_2CH_2$—O—$CH_2$—, —$CH_2$—S—$CH_2$—, —$CH_2$—S—$CH_2CH_2$—, —$CH_2CH_2$—S—$CH_2$—, —$CH_2$—NH—$CH_2$—, —$CH_2$—NH—$CH_2CH_2$—, —$CH_2CH_2$—NH—$CH_2$—, —$CH_2$—N$(CH_3)$—$CH_2$—, —$CH_2$—N$(CH_3)$—$CH_2$—$CH_2$— or —$CH_2$—$CH_2$—N$(CH_3)$—$CH_2$— and the number of the carbon atoms of the total of the numbers of the carbon atoms of the two radicals $A^1$ and $A^2$—$R^2$ is 6 to 20 carbon atoms.

7. A compound of formula (I) or salt thereof as claimed in claim 1, wherein $A^1$ is $CH_2CH_2$ or $CH_2CH_2CH_2$, $A^2$ is a direct bond, and $R^2$ is cyclobutyl.

8. A compound of formula (I) or salt thereof as claimed in claim 1, wherein $A^1$ is $CH_2CH_2CH_2$, $A^2$ is a direct bond, and $R^2$ is cyclopropyl or cyclobutyl.

9. A compound of formula (I) or salt thereof as claimed in claim wherein $A^1$ is $CH_2CH_2$ or $CH_2CH_2CH_2$, $A^2$ is $CH_2$, and $R^2$ is cyclopropyl unsubstituted or substituted with halogen or $(C_1–C_4)$alkyl, or is cyclobutyl unsubstituted or substituted with halogen or $(C_1–C_4)$alkyl.

10. A compound of formula (I) or salt thereof as claimed in claim 1, wherein $(X)_n$ is n substituents X, where the X in each case independently of one another are halogen, hydroxyl, amino, nitro, formyl, carboxyl, cyano, thiocyanato, aminocarbonyl or $(C_1–C_6)$alkyl, $(C_1–C_6)$alkoxy, $(C_1–C_6)$alkylthio, mono$(C_1–C_6)$alkylamino, di$(C_1–C_4)$alkylamino, $(C_2–C_6)$alkenyl, $(C_2–C_6)$alkynyl, $((C_1–C_6)$alkyl)carbonyl, $((C_1–C_6)$alkoxy)carbonyl, mono$(C_1–C_6)$alkylaminocarbonyl, di$(C_1–C_4)$alkylaminocarbonyl, N—$(C_1–C_6)$alkanoylamino or N—$(C_1–C_4)$alkanoyl-N—$(C_1–C_4)$alkylamino, each of the last-mentioned 13 radicals being unsubstituted or substituted by one or more radicals selected from the group consisting of halogen, hydroxyl, amino, nitro, formyl, carboxyl, cyano, thiocyanato, $(C_1–C_4)$alkoxy, $(C_1–C_4)$haloalkoxy, $(C_1–C_4)$alkylthio, $(C_1–C_4)$haloalkylthio, mono$(C_1–C_4)$alkylamino, di$(C_1–C_4)$alkylamino, $(C_3–C_9)$cycloalkyl, $(C_3–C_9)$cycloalkylamino, $((C_1–C_4)$alkyl)carbonyl, $((C_1–C_4)$alkoxy)carbonyl, aminocarbonyl, mono$(C_1–C_4)$alkylaminocarbonyl, di$(C_1–C_4)$alkylaminocarbonyl, phenyl, phenoxy, phenylthio, phenylcarbonyl, heterocyclyl, heterocyclyloxy, heterocyclylthio and heterocyclylamino, each of the last-mentioned 8 radicals being unsubstituted or having one or more substituents selected from the group consisting of halogen, nitro, cyano, $(C_1–C_4)$alkyl, $(C_1–C_4)$alkoxy, $(C_1–C_4)$alkylthio, $(C_1–C_4)$haloalkyl, $(C_1–C_4)$haloalkoxy, formyl, $(C_1–C_4)$alkylcarbonyl and $(C_1–C_4)$alkoxycarbonyl, or is $(C_3–C_9)$cycloalkyl, $(C_3–C_9)$cycloalkoxy, $(C_3–C_9)$cycloalkylamino, phenyl, phenoxy, phenylthio, phenylcarbonyl, heterocyclyl, heterocyclyloxy, heterocyclylthio or heterocyclylamino, each of the last-mentioned 11 radicals being unsubstituted or substituted.

11. A compound of formula (I) or salt thereof as claimed in claim 3, wherein the divalent or trivalent bridges of Group D) have 1 to 4 carbon atoms.

12. A compound of the formula (III) or an acid addition salt thereof:

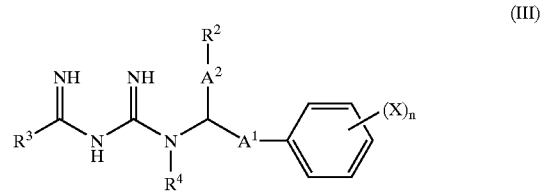

(III)

wherein $R^2$ is cyclopropyl, cyclobutyl, cyclopentyl or cyclohexyl, each of the last-mentioned four radicals being unsubstituted or substituted, or is $(C_4–C_9)$cycloalkenyl which is unsubstituted or substituted, or is heterocyclyl which is unsubstituted or substituted, $R^3$ is hydrogen, $(C_1–C_6)$alkyl, aryl or $(C_3–C_9)$cycloalkyl, each of the last-mentioned 3 radicals being unsubstituted or substituted, or a radical of the formula —N$(B^1$-$D^1)(B^2$-$D^2)$ or —NR'—N$(B^1$-$D^1)(B^2$-$D^2)$ in which $B^1$, $B^2$, $D^1$ and $D^2$ are in each case as defined below and wherein $R^1$=hydrogen, $(C_1–C_6)$alkyl or $((C_1–C_4)$alkyl)carbonyl and $R^1$ is unsubstituted or substituted $(C_1–C_6)$alkyl, aryl, aryl-$(C_1–C_6)$alkyl, $(C_3–C_9)$cycloalkyl or $(C_3–C_9)$cycloalkyl-$(C_1–C_6)$alkyl, $R^4$ is a radical of the formula -$B^3$-$D^3$, $B^3$ and $D^3$ being as defined below, $A^1$ is straight-chain alkylene having 1 to 5 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^4$-$D^4$, $B^4$ and $D^4$ being as defined below, $A^2$ is a direct bond or straight-chain alkylene having 1 to 4 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^5$-$D^5$ or a divalent radical of the formula $V^1$, $V^2$, $V^3$, $V^4$ or $V^5$, $$—CR^6R^7—W^*—CR^8R^9— \qquad (V^1)$$

$$—CR^{10}R^{11}—W^*—CR^{12}R^{13}—CR^{14}R^{15}— \qquad (V^2)$$

$$—CR^{16}R^{17}—CR^{18}R^{19}—W^*—CR^{20}R^{21}— \qquad (V^3)$$

$$—CR^{22}R^{23}—CR^{24}R^{25}—W^*— \qquad (V^4)$$

$$—CR^{26}R^{27}—W^* \qquad (V^5)$$

each of the radicals $R^6$ to $R^{27}$ in each case independently of one another being hydrogen, halogen, nitro, cyano, thiocyanato or a radical of the formula -$B^6$-$D^6$, $W^*$ is in each case an oxygen atom, a sulfur atom or a group of the formula —NH— or —N($CH_3$)—, and $B^5$, $B^6$, $B^7$, $D^5$ and $D^6$ are as defined below, $B^1$, $B^2$ and $B^3$ in each case independently of one another are a direct bond or a divalent group of formulae —C(=$Z^*$)—, —C(=$Z^*$)—$Z^{**}$—, —C(=$Z^*$)—NH— or —C(=$Z^*$)N$R^*$, $Z^*$ being an oxygen or sulfur atom, $Z^{**}$ an oxygen or sulfur atom and $R^*$ ($C_1$–$C_6$)alkyl, aryl, aryl-($C_1$–$C_6$)alkyl, ($C_3$–$C_9$) cycloalkyl or ($C_3$–$C_9$)cycloalkyl-($C_1$–$C_6$)alkyl, each of the 5 last-mentioned radicals being unsubstituted or substituted, $B^4$, $B^5$ and $B^6$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —N$R^o$—, —O—N$R^o$—, —N$R^o$—O—, —N$R^o$—CO—, —CO—N$R^o$—, —O—CO—N$R^o$— or —N$R^o$—CO—O—, p being the integer 0, 1 or 2 and $R^o$ being hydrogen, ($C_1$–$C_6$)alkyl, aryl, aryl-($C_1$–$C_6$)alkyl, ($C_3$–$C_9$)cycloalkyl or ($C_3$–$C_9$)cycloalkcyl-($C_1$–$C_6$)alkyl, each of the 5 last-mentioned radicals being unsubstituted or substituted, $D^1$, $D^2$, $D^3$, $D^4$, $D^5$ and $D^6$ in each case independently of one another are hydrogen, ($C_1$–$C_6$)alkyl, aryl, aryl-($C_1$–$C_6$)alkyl, ($C_3$–$C_9$)cycloalkyl or ($C_3$–$C_9$)cycloalkyl-($C_1$–$C_6$)alkyl, each of the 5 last-mentioned radicals being unsubstituted or substituted, or in each case two radicals $D^5$ of two groups -$B^5$-$D^5$ which are bonded to a carbon atom are linked to each other and form an alkylene group having 2 to 4 carbon atoms, this alkylene group being unsubstituted or substituted by one or more radicals selected from the group consisting of ($C_1$–$C_4$)alkyl and ($C_1$–$C_4$)alkoxy, $(X)_n$ is n substituents X, where the X in each case independently of one another are halogen, hydroxyl, amino, nitro, formyl, carboxyl, cyano, thiocyanato, aminocarbonyl or ($C_1$–$C_6$)alkyl, ($C_1$–$C_6$)alkoxy, ($C_1$–$C_6$)alkylthio, mono($C_1$–$C_6$)alkylamino, di($C_1$–$C_4$) alkylamino, ($C_2$–$C_6$)alkenyl, ($C_2$–$C_6$)alkynyl, (($C_1$–$C_6$) alkyl)carbonyl, (($C_1$–$C_6$)alkoxy)carbonyl, mono ($C_1$–$C_6$)alkylaminocarbonyl, di($C_1$–$C_4$) alkylaminocarbonyl, N-($C_1$–$C_6$)alkanoylamino or N—($C_1$–$C_4$)alkanoyl-N—($C_1$–$C_4$)alkylamino, each of the last-mentioned 13 radicals being unsubstituted or substituted, or two adjacent radicals X together are a fused cycle which has 4 to 6 ring atoms and is carbocyclic or which contains hetero ring atoms selected from the group consisting of O, S and N and which is unsubstituted or substituted by one or more radicals selected from the group consisting of halogen, ($C_1$–$C_4$)alkyl and oxo, n is 0, 1, 3, 4 or 5.

13. A compound of the formula (V) or an acid addition salt thereof:

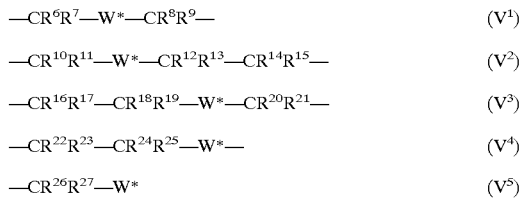

(V)

wherein $R^2$ is cyclopropyl, cyclobutyl, cyclopentyl or cyclohexyl, each of the last-mentioned four radicals being unsubstituted or substituted, or is ($C_4$–$C_9$)cycloalkenyl which is unsubstituted or substituted, or is heterocyclyl which is unsubstituted or substituted, $R^3$ is hydrogen, ($C_1$–$C_6$)alkyl, aryl or ($C_3$–$C_9$)cycloalkyl, each of the last-mentioned 3 radicals being unsubstituted or substituted, or a radical of the formula —N($B^1$-$D^1$)($B^2$-$D^2$) or —N'—($B^1$-$D^1$)($B^2$-$D^2$) in which $B^1$, $B^2$, $D^1$ and $D^2$ are in each case as defined below and wherein $R^1$=hydrogen, ($C_1$–$C_6$)alkyl or (($C_1$–$C_4$)alkyl) carbonyl and R' is unsubstituted or substituted ($C_1$–$C_6$) alkyl, aryl, aryl-($C_1$–$C_6$)alkyl, ($C_3$–$C_9$)cycloalkyl or ($C_3$–$C_9$)cycloalkyl-($C_1$–$C_6$)alkyl, $R^4$ is a radical of the formula -$B^3$-$D^3$, $B^3$ and $D^3$ being as defined below, $A^1$ is straight-chain alkylene having 1 to 5 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^4$-$D^4$, $B^4$ and $D^4$ being as defined below, $A^2$ is a direct bond or straight-chain alkylene having 1 to 4 carbon atoms or straight-chain alkenylene or alkynylene, each of which has 2 to 5 carbon atoms, each of the three last-mentioned divalent radicals being unsubstituted or substituted by one or more radicals selected from the group consisting of halogen, nitro, cyano, thiocyanato and radicals of the formula -$B^5$-$D^5$ or a divalent radical of the formula $V^1$, $V^2$, $V^3$, $V^4$ or $V^5$, $$—CR^6R^7—W^*—CR^8R^9— \qquad (V^1)$$

$$—CR^{10}R^{11}—W^*—CR^{12}R^{13}—CR^{14}R^{15}— \qquad (V^2)$$

$$—CR^{16}R^{17}—CR^{18}R^{19}—W^*—CR^{20}R^{21}— \qquad (V^3)$$

$$—CR^{22}R^{23}—CR^{24}R^{25}—W^*— \qquad (V^4)$$

$$—CR^{26}R^{27}—W^* \qquad (V^5)$$

each of the radicals $R^6$ to $R^{27}$ in each case independently of one another being hydrogen, halogen, nitro, cyano, thiocyanato or a radical of the formula -$B^6$-$D^6$, $W^*$ is in each case an oxygen atom, a sulfur atom or a group of the formula —NH— or —N($CH_3$)—, and $B^5$, $B^6$, $B^7$, $D^5$ and $D^6$ are as defined below, $B^1$, $B^2$ and $B^3$ in each case independently of one another are a direct bond or a divalent group of the formulae —C(=Z*)—, —C(=Z*)—Z**—, —C(=Z*)—NH— or —C(=Z*)NR*, Z* being an oxygen or sulfur atom, Z** an oxygen or sulfur atom and R* ($C_1$–$C_6$) alkyl, aryl, aryl-($C_1$–$C_6$)alkyl, ($C_3$–$C_9$) cycloalkyl or ($C_3$–$C_9$)cycloalkyl-($C_1$–$C_6$)alkyl, each of the 5 last-mentioned radicals being unsubstituted or substituted, $B^4$, $B^5$ and $B^6$ in each case independently of one another are a direct bond or a divalent group of the formulae —O—, —S(O)$_p$—, —S(O)$_p$—O—, —O—S(O)$_p$—, —CO—, —O—CO—, —CO—O—, —S—CO—, —CO—S—, —S—CS—, —CS—S—, —O—CO—O—, —NR°—, —O—NR°—, —NR°—O—, —NR°—CO—, —CO—NR°—, —O—CO—NR°— or —NR°—CO—O—, p being the integer 0, 1 or 2 and R° being hydrogen, ($C_1$–$C_6$)alkyl, aryl, aryl-($C_1$–$C_6$)alkyl, ($C_3$–$C_9$)cycloalkyl or ($C_3$–$C_9$)cycloallcyl-($C_1$–$C_6$)alkyl, each of the 5 last-mentioned radicals being unsubstituted or substituted, $D^1$, $D^2$, $D^3$, $D^4$, $D^5$ and $D^6$ in each case independently of one another are hydrogen, ($C_1$–$C_6$)alkyl, aryl, aryl-($C_1$–$C_6$)alkyl, ($C_3$–$C_9$)cycloalkyl or ($C_3$–$C_9$)cycloalkyl-($C_1$–$C_6$)alkyl, each of the 5 last-mentioned radicals being unsubstituted or substituted, or in each case two radicals $D^5$ of two groups -$B^5$-$D^5$ which are bonded to a carbon atom are linked to each other and form an alkylene group having 2 to 4 carbon atoms, this alkylene group being unsubstituted or substituted by one or more radicals selected from the group consisting of ($C_1$–$C_4$)alkyl and ($C_1$–$C_4$)alkoxy, (X)$_n$ is n substituents X, where the X in each case independently of one another are halogen, hydroxyl, amino, nitro, formyl, carboxyl, cyano, thiocyanato, aminocarbonyl or ($C_1$–$C_6$)alkyl, ($C_1$–$C_6$)alkoxy, ($C_1$–$C_6$)alkylthio, mono($C_1$–$C_6$)alkylamino, di($C_1$–$C_4$)alkylamino, ($C_2$–$C_6$)alkenyl, ($C_2$–$C_6$)alkynyl, (($C_1$–$C_6$)alkyl)carbonyl (($C_1$–$C_6$)alkoxy)carbonyl, mono($C_1$–$C_6$)alkylaminocarbonyl, di($C_1$–$C_4$)alkylaminocarbonyl, N—($C_1$–$C_6$)alkanoylamino or N—($C_1$–$C_4$)alkanoyl-N—($C_1$–$C_4$)alkylamino, each of the last-mentioned 13 radicals being unsubstituted or substituted, or two adjacent radicals X together are a fused cycle which has 4 to 6 ring atoms and is carbocyclic or which contains hetero ring atoms selected from the group consisting of O, S and N and which is unsubstituted or substituted by one or more radicals selected from the group consisting of halogen, ($C_1$–$C_4$)alkyl and oxo, n is 0, 1, 3, 4 or 5.

14. A compound as claimed in claim 12, wherein $A^1$ is $CH_2CH_2$ or $CH_2CH_2CH_2$, $A^2$ is a direct bond and $R^2$ is cyclobutyl.

15. A compound as claimed in claim 12, wherein $A^1$ is $CH_2CH_2CH_2$, $A^2$ is a direct bond and $R^2$ is cyclopropyl or cyclobutyl.

16. A compound as claimed in claim 13, wherein $A^1$ is $CH_2CH_2$ or $CH_2CH_2CH_2$, $A^2$ is a direct bond and $R^2$ is cyclobutyl.

17. A compound as claimed in claim 13, wherein $A^1$ is $CH_2CH_2$ or $CH_2CH_2CH_2$, $A^2$ is a direct bond and $R^2$ is cyclopropyl or cyclobutyl.

18. A process for the preparation of a compound of the formula (I) or a salt thereof as claimed in claim 1, which comprises a) reacting a compound of the formula (II)

where Fu is a functional group selected from the group consisting of carboxylic ester, carboxylic orthoester, carboxylic acid chloride, carboxamide, carboxylic anhydride and tichloromethyl with a biguanidide of the formula (III) or an acid addition salt thereof

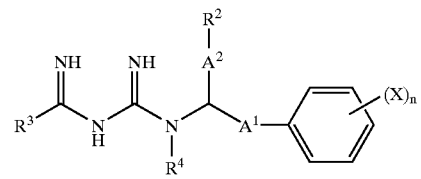

or b) reacting a compound of the formula (IV)

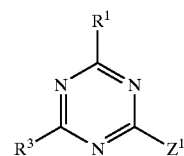

19. A herbicidal or plant-growth-regulating composition, which comprises one or more compounds of the formula (I) or salts thereof as claimed in claim 1 and formulation auxiliaries conventionally used in crop protection.

20. A method of controlling harmful plants or of regulating the growth of plants, wherein, an effective amount of one or more compounds of the formula (I) or salts thereof as claimed in claim 1 is applied to the plants, the seeds of the plants or the area under cultivation.

21. The method as claimed in claim 20, wherein the crop plants are transgenic crop plants.

* * * * *